United States Patent
Tian et al.

(10) Patent No.: US 10,933,038 B2
(45) Date of Patent: Mar. 2, 2021

(54) USE OF (BENZENESULFONAMIDO) BENZAMIDE COMPOUNDS FOR INHIBITING LIVER FIBROSIS

(71) Applicants: Hebei Medfaith Pharmaceutical Technology Co., Ltd., Shijiazhuang (CN); Institute of Medicinal Biotechnology, Chinese Academy of Medical Sciences, Beijing (CN)

(72) Inventors: Hongwei Tian, Shenyang (CN); Xingang Wang, Shenyang (CN); Rongguang Shao, Beijing (CN); Yucheng Wang, Beijing (CN); Naren Li, Beijing (CN); Shi-Ying Cai, Cheshire, CT (US); Hongwei He, Beijing (CN); Juxian Wang, Beijing (CN); Shuangshuang Zhao, Beijing (CN); Maoxu Ge, Beijing (CN); Jinfeng Ren, Beijing (CN)

(73) Assignees: Hebei Medfaith Pharmaceutical Technology Co., Ltd., Shijiazhuang (CN); Institute of Medicinal Biotechnology, Chinese Academy of Medical Sciences, Beijing (CN)

( * ) Notice: Subject to any disclaimer, the term of this patent is extended or adjusted under 35 U.S.C. 154(b) by 0 days.

(21) Appl. No.: 15/779,431

(22) PCT Filed: Nov. 24, 2016

(86) PCT No.: PCT/CN2016/107013
§ 371 (c)(1),
(2) Date: May 25, 2018

(87) PCT Pub. No.: WO2017/088775
PCT Pub. Date: Jun. 1, 2017

(65) Prior Publication Data
US 2018/0333376 A1   Nov. 22, 2018
US 2019/0274979 A2   Sep. 12, 2019

(30) Foreign Application Priority Data
Nov. 25, 2015   (CN) .......................... 201510830392.9

(51) Int. Cl.
A61K 31/63      (2006.01)
A61K 31/18      (2006.01)
A61P 1/16       (2006.01)
A61K 31/235     (2006.01)

(52) U.S. Cl.
CPC ............ *A61K 31/18* (2013.01); *A61K 31/235* (2013.01); *A61K 31/63* (2013.01); *A61P 1/16* (2018.01)

(58) Field of Classification Search
CPC ............ A61K 31/18; A61K 31/63; A61P 1/16
See application file for complete search history.

(56) References Cited

FOREIGN PATENT DOCUMENTS

| CN | 103183623   | * | 7/2013 |
| CN | 103183623 A |   | 7/2013 |
| CN | 105395532 A |   | 3/2016 |
| WO | WO 2004/032716 A2 |   | 4/2004 |
| WO | WO 2012064266 | * | 5/2012 |

OTHER PUBLICATIONS

International Search Report and Written Opinion for PCT/CN2016/107013, dated Nov. 25, 2015.
Amin et al., Characterization of ANIT-induced toxicity using precision-cut rat and dog liver slices cultured in a dynamic organ roller system. Toxicol Pathol. 2006;34(6):776-84.
Lin et al., Virus-related liver cirrhosis: molecular basis and therapeutic options. World J Gastroenterol. Jun. 7, 2014;20(21):6457-69. doi: 10.3748/wjg.v20.i21.6457. Review.
Novo et al., Cellular and molecular mechanisms in liver fibrogenesis. Arch Biochem Biophys. Apr. 15, 2014;548:20-37. doi: 10.1016/j.abb.2014.02.015. Epub Mar. 11, 2014. Review.
Zhang et al., Liver fibrosis and hepatic stellate cells: Etiology, pathological hallmarks and therapeutic targets. World J Gastroenterol. Dec. 28, 2016;22(48):10512-10522. doi: 10.3748/wjg.v22.i48.10512. Review.

* cited by examiner

*Primary Examiner* — Shobha Kantamneni
(74) *Attorney, Agent, or Firm* — Wolf, Greenfield & Sacks, P.C.

(57) ABSTRACT

The invention belongs to the technical field of medicines. In particular, the invention relates to use of (benzenesulfonamido) benzamide compounds for inhibiting liver fibrosis, or preventing and/or treating a liver injury, or improving a liver function, or preventing and/or treating a liver disease associated with liver fibrosis, for modulating (e.g. reducing) the content of collagen (e.g. type I collagen) in liver tissue, for modulating (e.g. inhibiting) the activity of COL1A1 promoter in a cell, and for modulating (e.g. inhibiting) expression level of a gene associated with liver fibrosis in a cell.

4 Claims, 5 Drawing Sheets
Specification includes a Sequence Listing.

SEQUENCE LISTING

```
<160> NUMBER OF SEQ ID NOS: 1

<210> SEQ ID NO 1
<211> LENGTH: 2436
<212> TYPE: DNA
<213> ORGANISM: homo sapiens

<400> SEQUENCE: 1
gtgggaaagc ctggatggga aacatatggg gaggggcggg gagctgcagg caggagccct      60
tcttactacg aaaacccaag aagcaaggaa gtggacaggt cactaaccct catactacca     120
agccctgcgg caccctgccc tagaccacca ctctaaatgt ctgttccctc caaaaacagg     180 accctgtcg cctattaggg aggggttctc ttggaactga cccacagtag ggggcaggac      240
tttggtgggt tcaagaactg ccatctcagc acctcagccc cctagtcctg ccctgcagtc     300
gctggcacta ggcgggggca gaccctgggc cacaagttgc tgccacatgg tcgggataat     360
tgatgaaggt ccatccctcc attgctgtct ccagccctgc ctctctggaa actctatatt     420
ttccctttaa ttatagcccc tgcagtctcc ctctgctgcc ccacccgcac cgctcatcct     480
ggctgcccac ggccagccgg ccagccgacg tggctccctc cccttctgtt cctttttttt     540
cccctttgcc ttcgttgcac aaaaccagct gggggagggc gtggagaggg gcgggggggag    600 gcaatggaat cttggatggt ttgggggagg cgggactccc cgcttccacg tttgcagctc     660
tggagcaccc ggggtgggga gctgcacagg agggagagaa atgaacaggg cactgcaagg     720 agaccccag gccttctctc agccctacag agtttctcag gacgaggtag attggggttg      780
aggcagagcc ttgttggggg aatgggacat ggaggaagaa aggacgtgga gttctagagc     840
catcttcctt agatatagcc tgctgtcctt cgggtcccca gacccttcca gagtgtacag     900
atgattctct ctggttccta aggcatagag caatgaccgg gattttcaag aaagagatga     960
ggcagtggga agtagcccct aaaacaaagt caatcatcct ctgcagccca tcccacaccc    1020
ccaaaggaaa gtttcaccca gacacccaaa atatcccata catccccaac actgagtcca    1080
ggtacaactg gagaagggc tttatgcagc tcccagaaag acacccctt agctaagtgc      1140 cctccctcca cccaggttct ctctggtttg actgtgctgg aaggagggt ctctaagcag     1200 cccctggcca cagccatggc aaacaaaact cttctctaag tcaccaatga tcacaggcct    1260
cccactaaaa atacttccca actctggggt ggaagagttt gggggatgaa ttttttagggg   1320 attgcaagcc ccaatcccca cctctgtgtc cctagaatcc cccacccta ccttggctgc     1380 tccatcaccc aaccaccaaa gctttcttct gcagaggcca cctagtcatg tttctcaccc    1440
```

```
tgcacctcag cctccccact ccatctctca atcatgccta gggtttggag gaaggcattt    1500
gattctgttc tggagcacag cagaagaatt gacatcctca aaattaaaac tcccttgcct    1560
gcacccctcc ctcagatatc tgattcttaa tgtctagaaa ggaatctgta aattgttccc    1620
caaatattcc taagctccat cccctagcca caccagaaga cacccccaaa caggcacatc    1680
tttttaattc ccagcttcct ctgttttgga gaggtcctca gcatgcctct ttatgcccct    1740
cccttagctc ttgccaggat atcagagggt gactggggca cagccaggag gaccccctcc    1800
ccaacacccc caaccttcc acctttggaa gtctccccac ccagctcccc agttccccag     1860
ttccacttct tctagattgg aggtcccagg aagagagcag aggggcaccc ctacccactg    1920
gttagcccac gccattctga ggacccagct gcaccccta cacagcacct ctggcccagg     1980
ctgggctggg gggctgggga ggcagagctg cgaagagggg agatgtgggg tggactccct    2040
tccctcctcc tcccctctc cattccaact cccaaattgg gggccgggcc aggcagctct     2100
gattggctgg ggcacgggcg gccggctccc cctctccgag gggcagggtt cctccctgct    2160
ctccatcagg acagtataaa aggggcccgg gccagtcgtc ggagcagacg ggagtttctc    2220
ctcggggtcg gagcaggagg cacgcggagt gtgaggccac gcatgagcgg acgctaaccc    2280
cctccccagc cacaaagagt ctacatgtct agggtctaga catgttcagc tttgtggacc    2340
tccggctcct gctcctctta gcggccaccg ccctcctgac gcacggccaa gaggaaggcc    2400
aagtcgaggg ccaagacgaa gacagtaagt cccaaa                              2436
```

USE OF (BENZENESULFONAMIDO) BENZAMIDE COMPOUNDS FOR INHIBITING LIVER FIBROSIS

RELATED APPLICATIONS

This application is a national stage filing under 35 U.S.C. § 371 of International Patent Application Serial No. PCT/CN2016/107013, filed Nov. 24, 2016, which claims priority to Chinese Patent Application No. 201510830392.9, filed Nov. 25, 2015, the entire contents of each of which are incorporated herein by reference in their entirety.

TECHNICAL FIELD

The invention belongs to the technical field of medicines. In particular, the invention relates to use of (benzenesulfonamido) benzamide compounds for inhibiting liver fibrosis, or preventing and/or treating a liver injury, or improving a liver function, or preventing and/or treating a liver disease associated with liver fibrosis, for modulating (e.g. reducing) the content of collagen (e.g. type I collagen) in liver tissue, for modulating (e.g. inhibiting) the activity of COL1A1 promoter in a cell, and for modulating (e.g. inhibiting) expression level of a gene associated with liver fibrosis in a cell.

BACKGROUND ART

Chronic liver disease is an important problem that threatens human health. The number of people who die from chronic liver disease each year is close to 800,000. Acute or chronic liver injury will result in the development of liver fibrosis. Liver fibrosis is a pathological process of excessive deposition of diffuse extracellular matrix (ECM) in liver, especially the excessive deposition of alpha-1 type I collagen, and its cytological basis is the activation of hepatic stellate cells. Liver fibrosis is a repair response to liver injury in organism. Such a self-repair is not perfect. The further development of liver fibrosis will result in liver cirrhosis, liver failure and portal hypertension, and finally liver transplantation will be needed for the extension of life. A famous liver disease-expert, Rogking, proposed after conducting deep research on liver fibrosis that typical liver fibrosis was reversible, however, once it developed into the middle or late stage of liver cirrhosis, it could not be reversed. Liver fibrosis is a common pathological change in various chronic liver diseases, and is also a necessary pathological process in severe fatal diseases such as liver cirrhosis and liver cancer, therefore, it is of great significance in the treatment and prevention of various chronic liver diseases, liver cirrhosis and even liver cancer, to study how to control the progression of fibrosis.

With the deep research on the mechanism of development and pathological process of liver fibrosis, more and more potential targets against liver fibrosis have been found, such as TGF-β1 and its receptors, TIMP1, TLR4, integrin αv, cannabioniod receptor, endothelin A receptor, SMAD7, IL-11416, PDGF, FGF, VEGF, Toll-like receptor (TLR), AT1R, mTOR, etc. However, in addition to treatment against the cause of disease, only in China, two traditional Chinese medicines—Fufang Biejia Ruangan Tablet and Fuzheng Huayu Capsule are approved for the treatment of liver fibrosis, wherein Fufang Biejia Ruangan Tablet is undergoing phase IV clinical trial, and for Fuzheng Huayu capsule, its phase IV clinical trial been completed in China and its USA FDA clinical phase II trial has been passed. Except for them, there are no more drugs that have been approved for the treatment of liver fibrosis internationally.

China is a country with a high incidence of liver disease. Now, there are 120 million HBsAg carriers, and 30 million chronic HBV patients need to be treated. Among the patients with chronic HBV, about 12% may develop liver cirrhosis after 5 to 20 years. In addition, the incidence rate of hepatitis C, alcohol liver, fatty liver, drug-induced hepatitis and the like also increases year by year. Therefore, it is urgent to develop new drugs against liver fibrosis and for preventing and treating liver injury.

Contents of Invention

In the invention, unless otherwise specified, the scientific and technical terms used herein have the meanings as generally understood by a person skilled in the art. Moreover, the laboratory operations involved herein are the routine operations widely used in the corresponding fields. In addition, in order to better understand the invention, the definitions and explanations of the relevant terms are provided as follows.

The term "COL1A1" as used in the invention refers to Collagen Type I Alpha 1 Chain. The term "COL1A1 gene" as used in the invention refers to a gene capable of encoding COL1A1, the sequence of which is well known in the art, and can be found in various public databases (e.g. in NCBI data, a sequence with an accession number of NC-000017.11).

The term "COL1A1 promoter" as used in the invention refers to a promoter of COL1A1 gene, and its exemplary sequence can be found in, for example, about the first 2400 bp of the sequence with an accession number of NC-000017.11 in NCBI data. In the invention, when the sequence of COL1A1 promoter is mentioned, it is described by reference to the sequence set forth in SEQ ID NO: 1.

The term "$C_1$-$C_4$alkyl" as used in the invention represents a linear or branched alkyl containing 1-4 carbon atoms, including, for example, "$C_1$-$C_2$alkyl", "$C_1$-$C_3$alkyl", "$C_2$-$C_3$alkyl", "$C_2$-$C_4$alkyl", "$C_3$-$C_4$alkyl", etc., and its examples include, but are not limited to: methyl, ethyl, n-propyl, isopropyl, n-butyl, isobutyl, sec-butyl, tert-butyl. In some preferred embodiments of the invention, the $C_1$-$C_4$alkyl is $C_1$-$C_2$alkyl, such as methyl or ethyl.

The term "halo-" as used in the invention refers to substitution with a halogen atom, wherein the halogen atom is selected from the group consisting of fluorine atom, chlorine atom, bromine atom and iodine atom. In some preferred embodiments of the invention, the halogen atom is fluorine atom or chlorine atom.

The term "halo-$C_1$-$C_4$alkyl" as used in the invention refers to a group derived from the substitution of one or more (e.g. 2, 3 or 4) hydrogen atoms of $C_1$-$C_4$alkyl with one or more (e.g. 2, 3 or 4) halogen atoms, wherein the halogen atom and $C_1$-$C_4$alkyl have the same meanings as defined above.

In some preferred embodiments of the invention, the halo-$C_1$-$C_4$alkyl is halo-methyl or halo-ethyl.

In some preferred embodiments of the invention, the halo-$C_1$-$C_4$alkyl is fluoro-$C_1$-$C_4$alkyl. The fluoro-$C_1$-$C_4$alkyl refers to a group derived from the substitution of one or more (e.g. 2, 3 or 4) hydrogen atoms of $C_1$-$C_4$alkyl with one or more (e.g. 2, 3 or 4) fluorine atoms. In some preferred embodiments of the invention, the fluoro-$C_1$-$C_4$alkyl is fluoro-$C_1$-$C_2$alkyl.

In some preferred embodiments of the invention, the halo-$C_1$-$C_4$alkyl is monohalo-$C_1$-$C_4$alkyl, dihalo-$C_1$-$C_4$alkyl or trihalo-$C_1$-$C_4$alkyl. The terms "monohalo-$C_1$-$C_4$alkyl", "dihalo-$C_1$-$C_4$alkyl", and "trihalo-$C_1$-$C_4$alkyl" as used in the invention refers to a group derived from the substitution of 1, 2 or 3 hydrogen atoms of "$C_1$-$C_4$alkyl" with 1, 2 or 3 "halogen atoms".

The term "TGF-β1" as used in the invention refers to transforming growth factor-β1.

The term "MMP2" as used in the invention refers to matrix metalloproteinase 2.

The term "α-SMA" as used in the invention refers to α-smooth muscle actin.

The terms "TIMP1" and "TIMP2" as used in the invention refer to tissue inhibitor of metalloproteinase 1 and tissue inhibitor of metalloproteinase 2, respectively.

The term "SPP1" as used in the invention refers to secreted phosphoprotein 1.

The term "an effective amount" as used in the invention refers to an amount that is sufficient to achieve or at least partially achieve a desired effect. For example, "an effective amount for preventing a disease" refers to an amount that is sufficient to prevent, suppress or delay the development of a disease; "an effective amount for treating a disease" refers to an amount that is sufficient to cure or at least partially suppress a disease and its complications in a patient with the disease. The determination of such an effective amount is completely within the ability of a person skilled in the art. For example, an amount effective for a therapeutic use depends on the severity of a disease to be treated, general state of the immune system in a patient, general conditions of a patient, such as age, body weight and gender, administration means of drugs, additional therapies used simultaneously, and the like.

The inventor of the present application surprisingly found that (benzenesulfonamido) benzamide compounds can inhibit the activity of COL1A1 promoter in a cell, can reduce the content of type I collagen in liver tissue, and can be used to inhibit liver fibrosis; thereby providing the following invention:

In an aspect, the present application relates to use of (benzenesulfonamido) benzamide compounds (e.g. 2-(benzenesulfonamido) benzamide compounds) in the manufacture of a medicament for the protection of liver injury and for the prevention and treatment of liver fibrosis.

The present application provides use of a compound of Formula (I) for inhibiting liver fibrosis, or preventing and/or treating a liver injury, or improving a liver function, or preventing and/or treating a liver disease associated with liver fibrosis, or for manufacture of a medicament for inhibiting liver fibrosis, or preventing and/or treating a liver injury, or improving a liver function, or preventing and/or treating a liver disease associated with liver fibrosis;

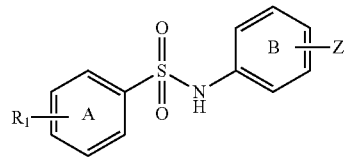

(I)

wherein
$R_1$ is selected from the group consisting of —O—($C_1$-$C_4$alkyl), halogen (e.g. —F, —$C_1$, —Br or —I), —NHCO—($C_1$-$C_4$alkyl), —CONH—($C_1$-$C_4$alkyl), —O-(halo-$C_1$-$C_4$alkyl) and —$NO_2$;

Z is —COO—($C_1$-$C_4$alkyl) or

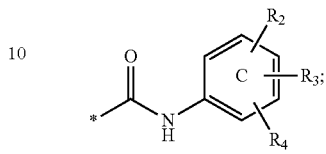

wherein $R_2$, $R_3$ and $R_4$ are each independently selected from the group consisting of —H, —O—($C_1$-$C_4$alkyl), halogen (e.g. —F, —$C_1$, —Br or —I), halo-$C_1$-$C_4$alkyl, —O-(halo-$C_1$-$C_4$alkyl), $C_1$-$C_4$alkyl and —OH.

In some preferred embodiments of the invention, $R_2$, $R_3$ and $R_4$ are not —H simultaneously.

In some preferred embodiments of the invention, in Ring A, $R_1$ is at the ortho-, meta- or para-position of —$SO_2$—.

In some preferred embodiments of the invention, $R_1$ is at the meta- or para-position of —$SO_2$—.

In some preferred embodiments of the invention, $R_1$ is at the meta-position of —$SO_2$—. In some preferred embodiments of the invention, $R_1$ is selected from the group consisting of —$OCH_3$, —$OCH_2CH_3$, halogen (e.g. —F, —$C_1$, —Br or —I), —$NHCOCH_3$, —$NHCOCH_2CH_3$, —$CONHCH_3$, —$CONHCH_2CH_3$, —$OCF_3$ and —$NO_2$.

In some preferred embodiments of the invention, $R_1$ is selected from the group consisting of —$OCH_3$, —F, —$C_1$, —$NHCOCH_3$, —$CONHCH_3$, —$OCF_3$ and —$NO_2$.

In some preferred embodiments of the invention, $R_1$ is selected from the group consisting of —$OCH_3$, —F, —$NHCOCH_3$, —$OCF_3$ and —$NO_2$.

In some preferred embodiments of the invention, $R_1$ is —$OCF_3$ or —$NO_2$.

In some preferred embodiments of the invention, in Ring B, Z is at the ortho-, meta- or para-position of —NH—.

In some preferred embodiments of the invention, Z is at the ortho- or meta-position of —NH—.

In some preferred embodiments of the invention, Z is at the ortho-position of —NH—.

In some preferred embodiments of the invention, Z is

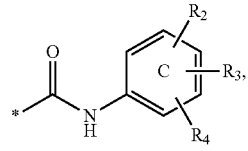

wherein $R_2$, $R_3$ and $R_4$ are each independently selected from the group consisting of —H, —$OCH_3$, —$OCH_2CH_3$, halogen (e.g. —F, —$C_1$, —Br or —I), halo-$C_1$-$C_2$alkyl, —O-(halo-$C_1$-$C_2$alkyl), —$CH_3$, —$CH_2CH_3$ and —OH.

In some preferred embodiments of the invention, $R_2$, $R_3$ and $R_4$ are each independently selected from the group consisting of —H, —$OCH_3$, —$OCH_2CH_3$, halogen (e.g. —F, —$C_1$, —Br or —I), fluoro-$C_1$-$C_2$alkyl, —O-(fluoro-$C_1$-$C_2$alkyl), —$CH_3$, —$CH_2CH_3$ and —OH.

In some preferred embodiments of the invention, $R_2$, $R_3$ and $R_4$ are each independently selected from the group consisting of —H, —$OCH_3$, —F, —$C_1$, —$CF_3$, —$OCF_3$, —$OCF_2H$ and —$CH_3$.

In some preferred embodiments of the invention, $R_2$, $R_3$ and $R_4$ are each independently selected from the group consisting of —H, —F, —$C_1$, —$CF_3$, —$OCF_3$, —$OCF_2H$ and —$CH_3$.

In some preferred embodiments of the invention, $R_2$, $R_3$ and $R_4$ are each independently selected from the group consisting of —H, —F, —$C_1$ and —$OCF_2H$.

In some preferred embodiments of the invention, $R_2$, $R_3$ and $R_4$ are each independently selected from the group consisting of —H and —$C_1$.

In some preferred embodiments of the invention, the compound has a structure of Formula (II):

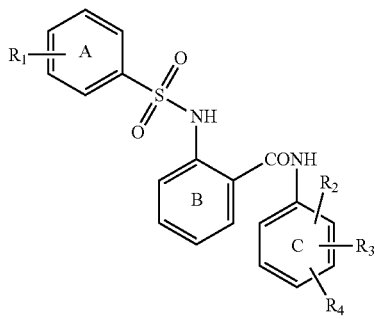

(II)

wherein
$R_1$ is at the meta- or para-position of —$SO_2$—;
$R_1$ is —$OCH_3$, —F, —$NHCOCH_3$, —$OCF_3$ or —$NO_2$;
$R_2$, $R_3$ and $R_4$ are each independently selected from the group consisting of —H, —F, —$C_1$ and —$OCF_2H$, and, $R_2$, $R_3$ and $R_4$ are not —H simultaneously.

In some preferred embodiments of the invention, $R_1$ is at the meta-position of —$SO_2$—.

In some preferred embodiments of the invention, $R_1$ is —$OCF_3$ or —$NO_2$.

In some preferred embodiments of the invention, $R_2$, $R_3$ and $R_4$ are each independently selected from the group consisting of —H and —$C_1$.

In some preferred embodiments of the invention, $R_1$ is at the meta-position of —$SO_2$—; $R_1$ is —$OCF_3$ or —$NO_2$; and, $R_2$, $R_3$ and $R_4$ are each independently selected from the group consisting of —H and —$C_1$.

In some preferred embodiments of the invention, $R_1$ is at the meta-position of —$SO_2$—; $R_1$ is —$OCH_3$, —F, —$NHCOCH_3$, —$OCF_3$ or —$NO_2$; $R_2$, $R_3$ and $R_4$ are each independently selected from the group consisting of —H, —$C_1$ and —$OCF_2H$.

In some preferred embodiments of the invention, Z is —$COOCH_3$.

In some preferred embodiments of the invention, in Ring A, $R_1$ is at the meta- or para-position of —$SO_2$—.

In some preferred embodiments of the invention, $R_1$ is —$NO_2$.

In some preferred embodiments of the invention, in Ring B, Z is at the ortho-position of —NH—.

In some preferred embodiments of the invention, Z is —$COOCH_3$; in Ring A, $R_1$ is at the meta- or para-position of —$SO_2$—; $R_1$ is —$NO_2$; and in Ring B, Z is at the ortho-position of —NH—.

In some preferred embodiments of the invention, the compound is selected from the compounds listed in Table 1:

TABLE 1

| Structure | Name | No. |
|---|---|---|
| 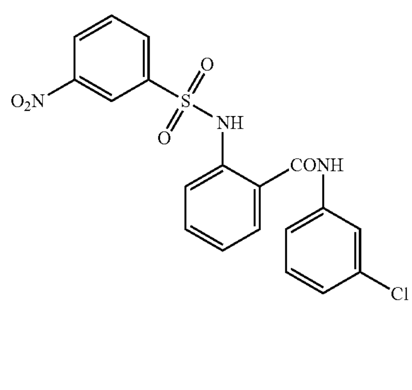 | N-(3-chlorophenyl)-2-(3-nitrobenzenesulfonamido)benzamide | 16-1 |
| 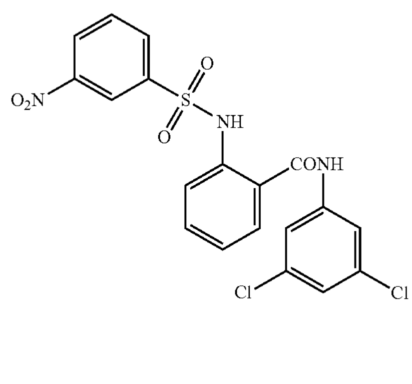 | N-(3,5-dichlorophenyl)-2-(3-nitrobenzenesulfonamide)benzamide | 16-2 |

TABLE 1-continued

| Structure | Name | No. |
|---|---|---|
| 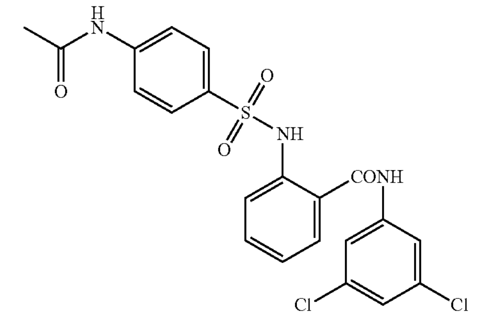 | N-(3,5-dichlorophenyl)-2-(4-acetamidobenzenesulfonamido)benzamide | 16-3 |
| 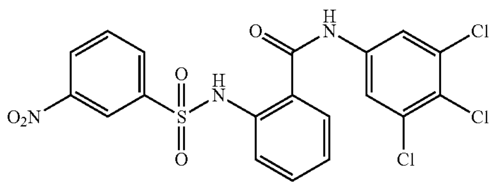 [SMILES: O=C(Nc1cc(Cl)c(Cl)c(Cl)c1)c1ccccc1NS(=O)(=O)c1cccc([N+](=O)[O-])c1] | N-(3,4,5-trichlorophenyl)-2-(3-nitrobenzenesulfonamido)benzamide | 16-4 |
| 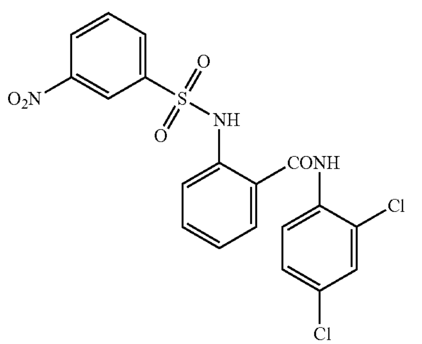 | N-(2,4-dichlorophenyl)-2-(3-nitorbenzenesulfonamido)benzamide | 16-5 |
| 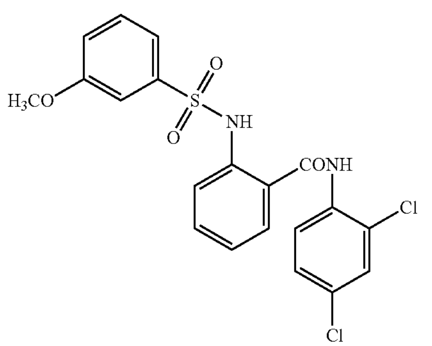 | N-(2,4-dichlorophenyl)-2-(3-methoxybenzenesulfonamido)benzamide | 16-6 |
| 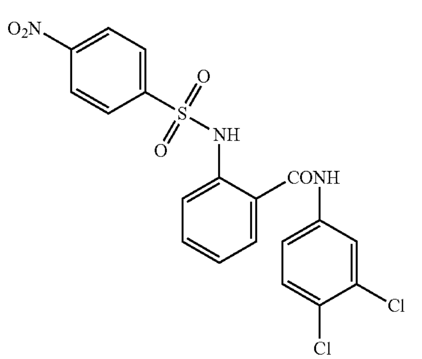 | N-(3,4-dichlorophenyl)-2-(4-nitorbenzenesulfonamido)benzamide | 16-7 |

TABLE 1-continued

| Structure | Name | No. |
|---|---|---|
| 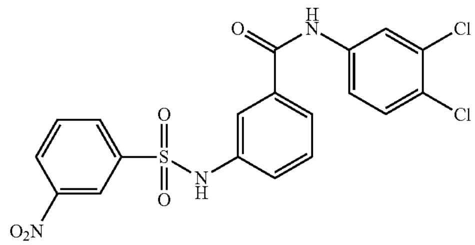 [SMILES: O=C(Nc1ccc(Cl)c(Cl)c1)c1cccc(NS(=O)(=O)c2cccc([N+](=O)[O-])c2)c1] | N-(3,4-dichlorophenyl)-3-(3-nitrobenzenesulfonamido)benzamide | 16-8 |
| 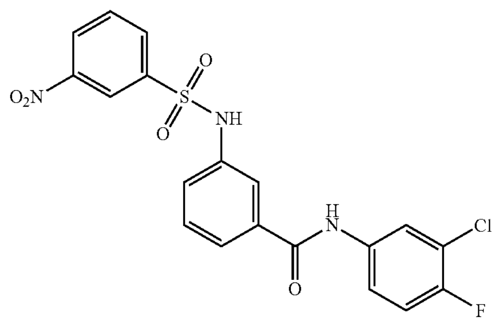 [SMILES: O=C(Nc1ccc(F)c(Cl)c1)c1cccc(NS(=O)(=O)c2cccc([N+](=O)[O-])c2)c1] | N-(3-chloro-4-fluorophenyl)-3-(3-nitrobenzenesulfonamido)benzamide | 17-9 |
| 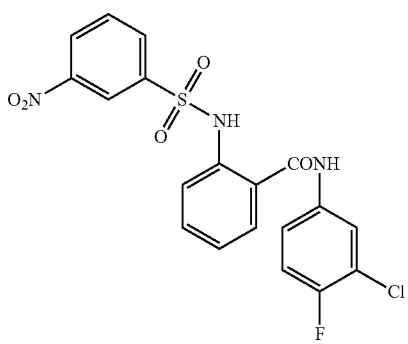 | N-(3-chloro-4-fluorophenyl)-2-(3-nitrobenzenesulfonamido)benzamide | 17-10 |
| 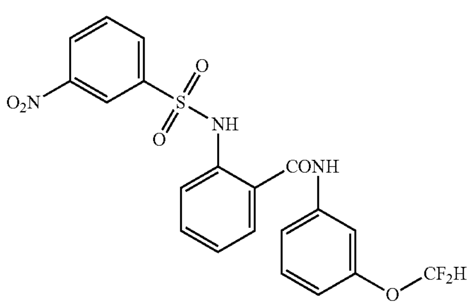 | N-(3-difluoromethoxyphenyl)-2-(3-nitrobenzenesulfonamido)benzamide | 17-11 |
| 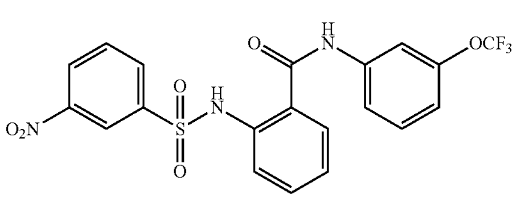 [SMILES: O=C(Nc1cccc(OC(F)(F)F)c1)c1ccccc1NS(=O)(=O)c1cccc([N+](=O)[O-])c1] | N-(3-trifluoromethoxyphenyl)-2-(3-nitrobenzenesulfonamido)benzamide | 17-12 |
| 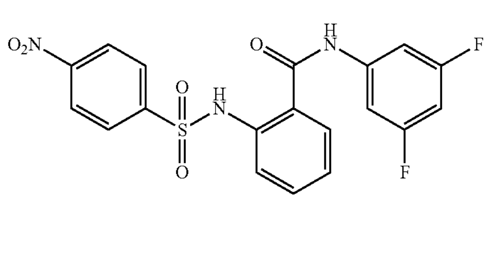 [SMILES: O=C(Nc1cc(F)cc(F)c1)c1ccccc1NS(=O)(=O)c1ccc([N+](=O)[O-])cc1] | N-(3,5-difluorophenyl)-2-(4-nitrobenzenesulfonamido)benzamide | 17-13 |

TABLE 1-continued

| Structure | Name | No. |
|---|---|---|
| 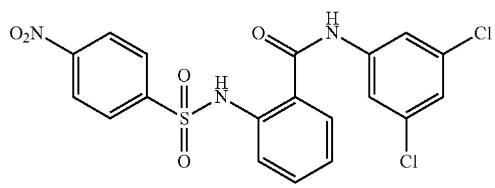 [SMILES: O=C(Nc1cc(Cl)cc(Cl)c1)c1ccccc1NS(=O)(=O)c1ccc([N+](=O)[O-])cc1] | N-(3,5-dichlorophenyl)-2-(4-nitrobenzenesulfonamido)benzamide | — |
| 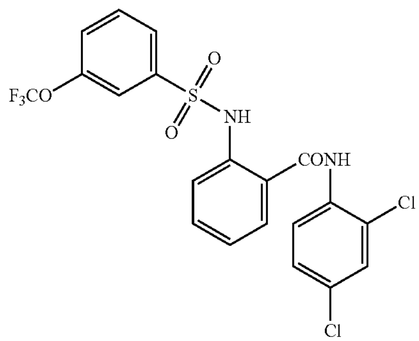 | N-(2,4-dichlorophenyl)-2-(3-trifluoromethoxybenzenesulfonamido)benzamide | 17-14 |
| 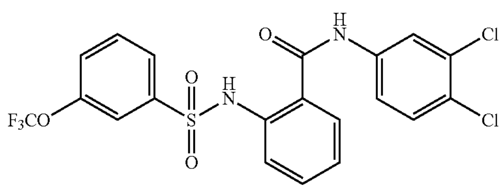 [SMILES: O=C(Nc1ccc(Cl)c(Cl)c1)c1ccccc1NS(=O)(=O)c1cccc(OC(F)(F)F)c1] | N-(3,4-dichlorophenyl)-2-(3-trifluoromethoxybenzenesulfonamido)benzamide | 17-15 |
| 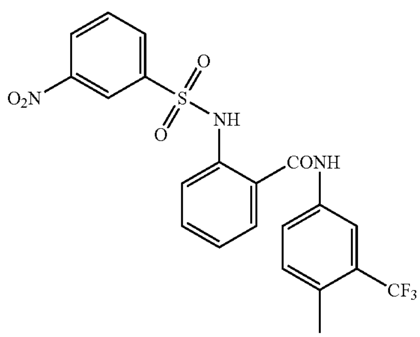 | N-(3-trifluoromethyl-4-methylphenyl)-2-(3-nitrobenzenesulfonamido)benzamide | 17-16 |
| 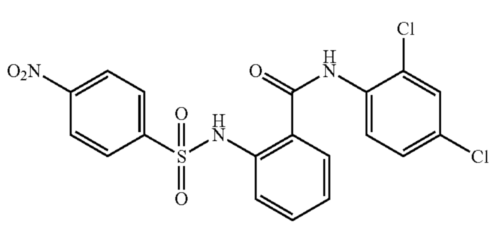 [SMILES: O=C(Nc1ccc(Cl)cc1Cl)c1ccccc1NS(=O)(=O)c1ccc([N+](=O)[O-])cc1] | N-(2,4-dichlorophenyl)-2-(4-nitrobenzenesulfonamido)benzamide | 17-17 |
| 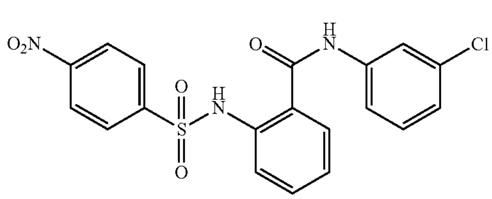 [SMILES: O=C(Nc1cccc(Cl)c1)c1ccccc1NS(=O)(=O)c1ccc([N+](=O)[O-])cc1] | N-(3-chlorophenyl)-2-(4-nitrobenzenesulfonamido)benzamide | 17-18 |

TABLE 1-continued

| Structure | Name | No. |
|---|---|---|
| 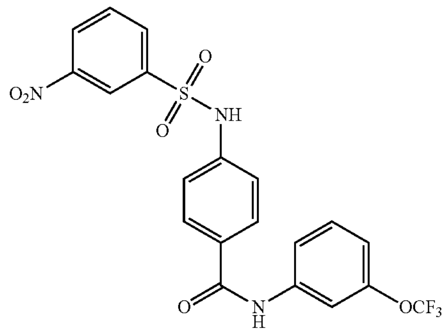 [SMILES: O=C(Nc1cccc(OC(F)(F)F)c1)c1ccc(NS(=O)(=O)c2cccc([N+](=O)[O-])c2)cc1] | N-(3-trifluoromethoxyphenyl)-4-(3-nitrobenzenesulfonamido)benzamide | 20-1 |
| 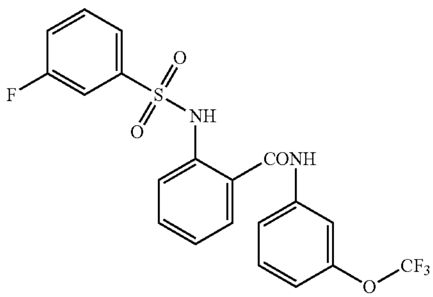 | N-(3-trifluoromethoxyphenyl)-2-(3-fluorobenzenesulfonamido)benzamide | 20-2 |
| 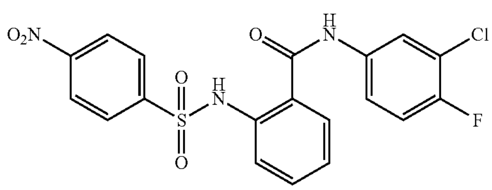 [SMILES: O=C(Nc1ccc(F)c(Cl)c1)c1ccccc1NS(=O)(=O)c1ccc([N+](=O)[O-])cc1] | N-(3-chloro-4-fluorophenyl)-2-(4-nitrobenzenesulfonamido)benzamide | 20-3 |
| 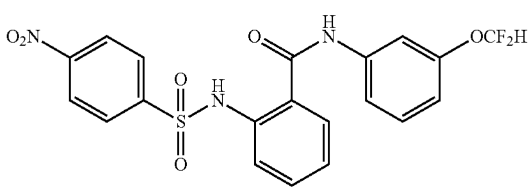 | N-(3-difluoromethoxyphenyl)-2-(4-nitrobenzenesulfonamido)benzamide | 20-4 |
| 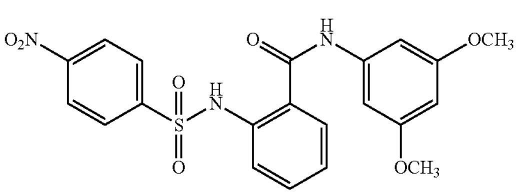 [SMILES: COc1cc(NC(=O)c2ccccc2NS(=O)(=O)c2ccc([N+](=O)[O-])cc2)cc(OC)c1] | N-(3,5-dimethoxyphenyl)-2-(4-nitrobenzenesulfonamido)benzamide | 20-5 |
| 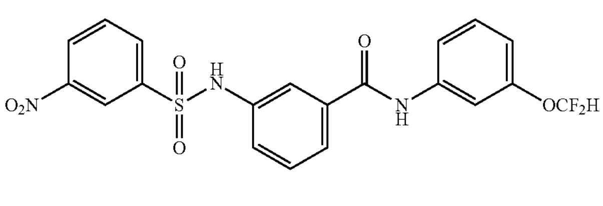 | N-(3-difluoromethoxyphenyl)-3-(3-nitrobenzenesulfonamido)benzamide | 20-6 |

TABLE 1-continued

| Structure | Name | No. |
|---|---|---|
| 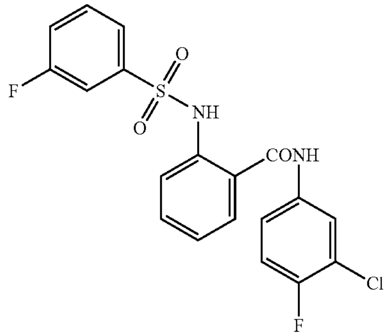 | N-(3-chloro-4-fluorophenyl)-2-(3-fluorobenzenesulfonamido)benzamide | 20-7 |
| 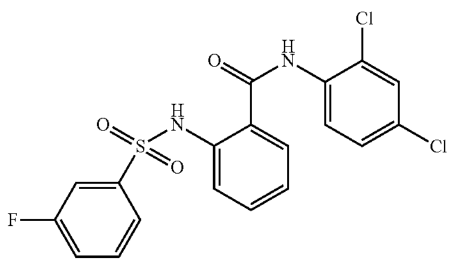 [SMILES: O=C(Nc1ccc(Cl)cc1Cl)c1ccccc1NS(=O)(=O)c1cccc(F)c1] | N-(2,4-dichlorophenyl)-2-(3-fluorobenzenefulfonamido)benzamide | 20-8 |
| 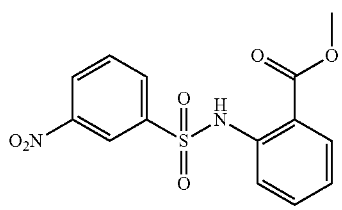 [SMILES: COC(=O)c1ccccc1NS(=O)(=O)c1cccc([N+](=O)[O-])c1] | methyl 2-(3-nitrobenzenesulfonamido)benzoate | 20-9 |
| 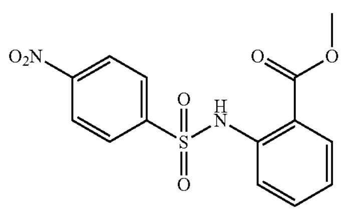 [SMILES: COC(=O)c1ccccc1NS(=O)(=O)c1ccc([N+](=O)[O-])cc1] | methyl 2-(4-nitrobenzenesulfonamido)benzoate | 20-10 |

In some preferred embodiments of the invention, a compound of Formula (I) is prepared by the method as disclosed in CN patent application CN103183623A.

In some preferred embodiments of the invention, the liver fibrosis is caused by a liver injury.

In some preferred embodiments of the invention, the liver injury is an acute liver injury or a chronic liver injury.

In some preferred embodiments of the invention, the liver injury is selected from the group consisting of a violence-caused liver injury (e.g. an open liver injury, a closed liver injury), a drug-induced liver injury, a toxic liver injury and a pathological liver injury (e.g. a liver injury caused by viral hepatitis, liver cancer or an autoimmune disease).

In some preferred embodiments of the invention, the liver disease associated with liver fibrosis is selected from the group consisting of: viral hepatitis (e.g. Hepatitis A, Hepatitis B, Hepatitis C, Hepatitis D, Hepatitis E), fatty liver, an autoimmune liver disease, a drug-induced liver disease, toxic hepatopathy and liver cancer.

In some preferred embodiments of the invention, the compound can inhibit bile duct proliferation and/or liver tissue necrosis.

In some preferred embodiments of the invention, the compound as an active ingredient, and a pharmaceutically acceptable carrier can form a pharmaceutical composition, for the protection of liver injury and for the prevention and treatment of liver fibrosis. In some preferred embodiments of the invention, the compound can also be used as main material, to prepare a health care product for the protection of liver injury and the prevention of liver fibrosis.

The pharmaceutical composition or health care product may be prepared into any pharmaceutically acceptable dosage form, such as an oral dosage form or a non-oral dosage form; for example, a tablet, a capsule, a pulvis, a pill, a granule, a solution, a suspension, a syrup, an injection (including injectio, sterile powder for injection and concentrated solution for injection), a suppository, an inhalent or an spraying agent.

The pharmaceutical composition or health care product may be administered to a patient or a subject in need thereof by any suitable route, such as orally, parenterally, rectally, intrapulmonarily or topically. When administered orally, the pharmaceutical composition or health care product may be prepared into an oral formulation, e.g. an oral solid formulation such as a tablet, a capsule, a pill, and a granule; or an oral liquid formulation, such as an oral solution, an oral suspension, and a syrup. When being prepared into an oral formulation, the pharmaceutical composition or health care product may also comprise a suitable filler, a binding agent, a disintegrating agent or a lubricant, etc. When administered parenterally, the pharmaceutical composition or health care product may be prepared into an injection, including injectio, sterile powder for injection and concentrated solution for injection. When being prepared into an injection, the pharmaceutical composition or health care product may be prepared by a conventional method existing in the pharmaceutical field. When preparing an injection, to the pharmaceutical composition or health care product, no additive may be added, or a suitable additive may be added depending on the property of drug. When administered rectally, the pharmaceutical composition or health care product may be a suppository, etc. When administered intrapulmonarily, the pharmaceutical composition or health care product may be an inhalent, or a spraying agent, etc.

In some preferred embodiments of the invention, the compound is present in a therapeutically and/or prophylactically effective amount in a pharmaceutical composition or a health care product. In some preferred embodiments of the invention, the compound is present in the form of a unit dose in a pharmaceutical composition or a health care product. In some preferred embodiments of the invention, the administration dose of the compound can be adjusted depending on factors such as pathogenic condition, age, body weight, and gender of a patient or subject, administration route and course of treatment.

In an aspect, the present invention provides use of a compound of Formula (I) for modulating (e.g. reducing) the content of collagen (e.g. type I collagen) in liver tissue, or for manufacture of a medicament for modulating (e.g. reducing) the content of collagen (e.g. type I collagen) in liver tissue;

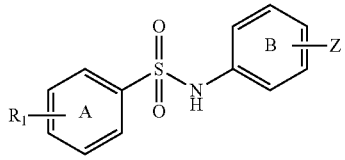

(I)

wherein $R_1$ is selected from the group consisting of —O—($C_1$-$C_4$alkyl), halogen (e.g. —F, —$C_1$, —Br or —I), —NHCO—($C_1$-$C_4$alkyl), —CONH—($C_1$-$C_4$alkyl), —O-(halo-$C_1$-$C_4$alkyl) and —$NO_2$;

Z is —COO—($C_1$-$C_4$alkyl) or

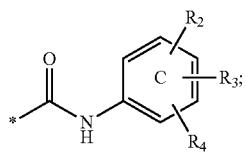

wherein $R_2$, $R_3$ and $R_4$ are each independently selected from the group consisting of —H, —O—($C_1$-$C_4$alkyl), halogen (e.g. —F, —$C_1$, —Br or —I), halo-$C_1$-$C_4$alkyl, —O-(halo-$C_1$-$C_4$alkyl), $C_1$-$C_4$alkyl and —OH.

In some preferred embodiments of the invention, $R_2$, $R_3$ and $R_4$ are not —H simultaneously.

In some preferred embodiments of the invention, in Ring A, $R_1$ is at the ortho-, meta- or para-position of —$SO_2$—.

In some preferred embodiments of the invention, $R_1$ is at the meta- or para-position of —$SO_2$—.

In some preferred embodiments of the invention, $R_1$ is at the meta-position of —$SO_2$—.

In some preferred embodiments of the invention, $R_1$ is selected from the group consisting of —$OCH_3$, —$OCH_2CH_3$, halogen (e.g. —F, —$C_1$, —Br or —I), —$NHCOCH_3$, —$NHCOCH_2CH_3$, —$CONHCH_3$, —$CONHCH_2CH_3$, —$OCF_3$ and —$NO_2$.

In some preferred embodiments of the invention, $R_1$ is selected from the group consisting of —$OCH_3$, —F, —$C_1$, —$NHCOCH_3$, —$CONHCH_3$, —$OCF_3$ and —$NO_2$.

In some preferred embodiments of the invention, $R_1$ is selected from the group consisting of —$OCH_3$, —F, —$NHCOCH_3$, —$OCF_3$ and —$NO_2$.

In some preferred embodiments of the invention, $R_1$ is —$OCF_3$ or —$NO_2$.

In some preferred embodiments of the invention, in Ring B, Z is at the ortho-, meta- or para-position of —NH—.

In some preferred embodiments of the invention, Z is at the ortho- or meta-position of —NH—.

In some preferred embodiments of the invention, Z is at the ortho-position of —NH—.

In some preferred embodiments of the invention, Z is

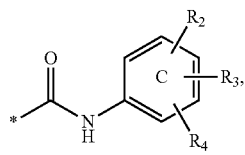

wherein $R_2$, $R_3$ and $R_4$ are each independently selected from the group consisting of —H, —$OCH_3$, —$OCH_2CH_3$, halogen (e.g. —F, —$C_1$, —Br or —I), halo-$C_1$-$C_2$alkyl, —O-(halo-$C_1$-$C_2$alkyl), —$CH_3$, —$CH_2CH_3$ and —OH.

In some preferred embodiments of the invention, $R_2$, $R_3$ and $R_4$ are each independently selected from the group consisting of —H, —$OCH_3$, —$OCH_2CH_3$, halogen (e.g. —F, —$C_1$, —Br or —I), fluoro-$C_1$-$C_2$alkyl, —O-(fluoro-$C_1$-$C_2$alkyl), —$CH_3$, —$CH_2CH_3$ and —OH.

In some preferred embodiments of the invention, $R_2$, $R_3$ and $R_4$ are each independently selected from the group consisting of —H, —$OCH_3$, —F, —$C_1$, —$CF_3$, —$OCF_3$, —$OCF_2H$ and —$CH_3$.

In some preferred embodiments of the invention, $R_2$, $R_3$ and $R_4$ are each independently selected from the group consisting of —H, —F, —$C_1$, —$CF_3$, —$OCF_3$, —$OCF_2H$ and —$CH_3$.

In some preferred embodiments of the invention, $R_2$, $R_3$ and $R_4$ are each independently selected from the group consisting of —H, —F, —$C_1$ and —$OCF_2H$.

In some preferred embodiments of the invention, $R_2$, $R_3$ and $R_4$ are each independently selected from the group consisting of —H and —$C_1$.

In some preferred embodiments of the invention, the compound has a structure of Formula (II):

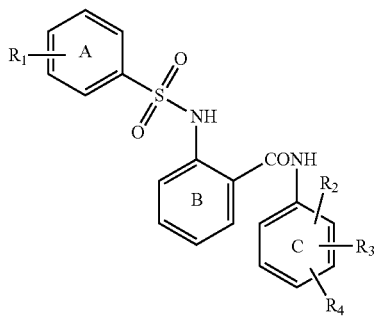

(II)

wherein $R_1$ is at the meta- or para-position of $-SO_2-$;

$R_1$ is $-OCH_3$, $-F$, $-NHCOCH_3$, $-OCF_3$ or $-NO_2$;

$R_2$, $R_3$ and $R_4$ are each independently selected from the group consisting of $-H$, $-F$, $-C_1$ and $-OCF_2H$, and, $R_2$, $R_3$ and $R_4$ are not $-H$ simultaneously.

In some preferred embodiments of the invention, $R_1$ is at the meta-position of $-SO_2-$.

In some preferred embodiments of the invention, $R_1$ is $-OCF_3$ or $-NO_2$.

In some preferred embodiments of the invention, $R_2$, $R_3$ and $R_4$ are each independently selected from the group consisting of $-H$ and $-C_1$.

In some preferred embodiments of the invention, $R_1$ is at the meta-position of $-SO_2-$; $R_1$ is $-OCF_3$ or $-NO_2$; and, $R_2$, $R_3$ and $R_4$ are each independently selected from the group consisting of $-H$ and $-C_1$.

In some preferred embodiments of the invention, $R_1$ is at the meta-position of $-SO_2-$; $R_1$ is $-OCH_3$, $-F$, $-NHCOCH_3$, $-OCF_3$ or $-NO_2$; $R_2$, $R_3$ and $R_4$ are each independently selected from the group consisting of $-H$, $-C_1$ and $-OCF_2H$.

In some preferred embodiments of the invention, Z is $-COOCH_3$.

In some preferred embodiments of the invention, in Ring A, $R_1$ is at the meta- or para-position of $-SO_2-$.

In some preferred embodiments of the invention, $R_1$ is $-NO_2$.

In some preferred embodiments of the invention, in Ring B, Z is at the ortho-position of $-NH-$.

In some preferred embodiments of the invention, Z is $-COOCH_3$; in Ring A, $R_1$ is at the meta- or para-position of $-SO_2-$; $R_1$ is $-NO_2$; and in Ring B, Z is at the ortho-position of $-NH-$.

In some preferred embodiments of the invention, the compound is selected from the compounds listed in Table 1.

In some preferred embodiments of the invention, the compound as active ingredient, and a pharmaceutically acceptable carrier form a pharmaceutical composition, for modulating (e.g. reducing) the content of collagen (e.g. type I collagen) in liver tissue. The pharmaceutical composition may be prepared into any pharmaceutically acceptable dosage form, such as an oral dosage form or a non-oral dosage form; for example, a tablet, a capsule, a pulvis, a pill, a granule, a solution, a suspension, a syrup, an injection (including injectio, sterile powder for injection and concentrated solution for injection), a suppository, an inhalant or an spraying agent.

The pharmaceutical composition may also be administered to a patient or a subject in need thereof by any suitable route, such as orally, parenterally, rectally, intrapulmonarily or topically. When administered orally, the pharmaceutical composition may be prepared into an oral formulation, e.g. an oral solid formulation such as a tablet, a capsule, a pill, and a granule; or an oral liquid formulation, such as an oral solution, an oral suspension, and a syrup. When being prepared into an oral formulation, the pharmaceutical composition may also comprise a suitable filler, binding agent, disintegrating agent or lubricant, etc. When administered parenterally, the pharmaceutical composition may be prepared into an injection, including injectio, sterile powder for injection and concentrated solution for injection. When being prepared into an injection, the pharmaceutical composition may be prepared by a conventional method existing in the pharmaceutical field. When preparing an injection, to the pharmaceutical composition, no additive may be added, or a suitable additive may be added depending on the property of drug. When administered rectally, the pharmaceutical composition may be prepared into a suppository, etc. When administered intrapulmonarily, the pharmaceutical composition may be prepared into an inhalant, or a spraying agent, etc.

In some preferred embodiments of the invention, the compound is present in a therapeutically and/or prophylactically effective amount in a pharmaceutical composition. In some preferred embodiments of the invention, the compound is present in the form of a unit dose in a pharmaceutical composition. In some preferred embodiments of the invention, the administration dose of the compound can be adjusted depending on factors such as pathogenic condition, age, body weight, and gender of a patient or subject, administration route and course of treatment.

In an aspect, the present application provides use of a compound of Formula (I) for modulating (e.g. inhibiting) the activity of COL1A1 promoter in a cell, or for manufacture of an agent for modulating (e.g. inhibiting) the activity of COL1A1 promoter in a cell;

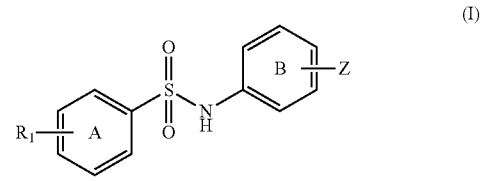

(I)

wherein $R_1$ is selected from the group consisting of $-O-(C_1-C_4\text{alkyl})$, halogen (e.g. $-F$, $-C_1$, $-Br$ or $-I$), $-NHCO-(C_1-C_4\text{alkyl})$, $-CONH-(C_1-C_4\text{alkyl})$, $-O-(halo-C_1-C_4\text{alkyl})$ and $-NO_2$;

Z is $-COO-(C_1-C_4\text{alkyl})$ or

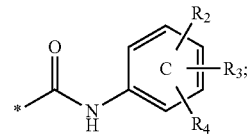

wherein $R_2$, $R_3$ and $R_4$ are each independently selected from the groups consisting of $-H$, $-O-(C_1-C_4\text{alkyl})$, halogen (e.g. —F, —C₁, —Br or —I), halo-$C_1$-$C_4$alkyl, —O-(halo-$C_1$-$C_4$alkyl), $C_1$-$C_4$alkyl and —OH.

In some preferred embodiments of the invention, $R_2$, $R_3$ and $R_4$ are not —H simultaneously.

In some preferred embodiments of the invention, in Ring A, $R_1$ is at the ortho-, meta- or para-position of —$SO_2$—.

In some preferred embodiments of the invention, $R_1$ is at the meta- or para-position of —$SO_2$—.

In some preferred embodiments of the invention, $R_1$ is at the meta-position of —$SO_2$—.

In some preferred embodiments of the invention, $R_1$ is selected from the group consisting of —$OCH_3$, —$OCH_2CH_3$, halogen (e.g. —F, —C₁, —Br or —I), —$NHCOCH_3$, —$NHCOCH_2CH_3$, —$CONHCH_3$, —$CONHCH_2CH_3$, —$OCF_3$ and —$NO_2$.

In some preferred embodiments of the invention, $R_1$ is selected from the group consisting of —$OCH_3$, —F, —C₁, —$NHCOCH_3$, —$CONHCH_3$, —$OCF_3$ and —$NO_2$.

In some preferred embodiments of the invention, $R_1$ is selected from the group consisting of —$OCH_3$, —F, —$NHCOCH_3$, —$OCF_3$ and —$NO_2$.

In some preferred embodiments of the invention, $R_1$ is —$OCF_3$ or —$NO_2$.

In some preferred embodiments of the invention, in Ring B, Z is at the ortho-, meta- or para-position of —NH—.

In some preferred embodiments of the invention, Z is at the ortho- or meta-position of —NH—.

In some preferred embodiments of the invention, Z is at the ortho-position of —NH—.

In some preferred embodiments of the invention, Z is

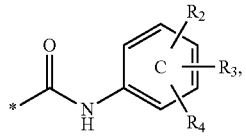

wherein $R_2$, $R_3$ and $R_4$ are each independently selected from the group consisting of —H, —$OCH_3$, —$OCH_2CH_3$, halogen (e.g. —F, —C₁, —Br or —I), halo-$C_1$-$C_2$alkyl, —O-(halo-$C_1$-$C_2$alkyl), —$CH_3$, —$CH_2CH_3$ and —OH.

In some preferred embodiments of the invention, $R_2$, $R_3$ and $R_4$ are each independently selected from the group consisting of —H, —$OCH_3$, —$OCH_2CH_3$, halogen (e.g. —F, —C₁, —Br or —I), fluoro-$C_1$-$C_2$alkyl, —O-(fluoro-$C_1$-$C_2$alkyl), —$CH_3$, —$CH_2CH_3$ and —OH.

In some preferred embodiments of the invention, $R_2$, $R_3$ and $R_4$ are each independently selected from the group consisting of —H, —$OCH_3$, —F, —C₁, —$CF_3$, —$OCF_3$, —$OCF_2H$ and —$CH_3$.

In some preferred embodiments of the invention, $R_2$, $R_3$ and $R_4$ are each independently selected from the group consisting of —H, —F, —C₁, —$CF_3$, —$OCF_3$, —$OCF_2H$ and —$CH_3$.

In some preferred embodiments of the invention, $R_2$, $R_3$ and $R_4$ are each independently selected from the group consisting of —H, —F, —C₁ and —$OCF_2H$.

In some preferred embodiments of the invention, $R_2$, $R_3$ and $R_4$ are each independently selected from the group consisting of —H and —C₁.

In some preferred embodiments of the invention, the compound has a structure of Formula (II):

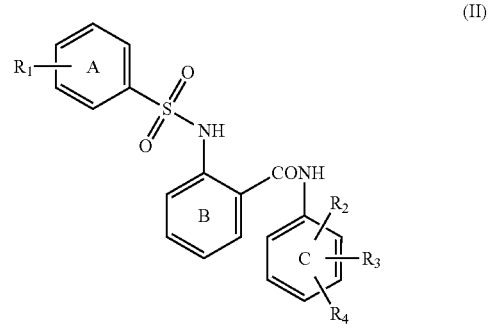

wherein
$R_1$ is at the meta- or para-position of —$SO_2$—;
$R_1$ is —$OCH_3$, —F, —$NHCOCH_3$, —$OCF_3$ or —$NO_2$;
$R_2$, $R_3$ and $R_4$ are each independently selected from the group consisting of —H, —F, —C₁ and —$OCF_2H$, and, $R_2$, $R_3$ and $R_4$ are not —H simultaneously.

In some preferred embodiments of the invention, $R_1$ is at the meta-position of —$SO_2$—.

In some preferred embodiments of the invention, $R_1$ is —$OCF_3$ or —$NO_2$.

In some preferred embodiments of the invention, $R_2$, $R_3$ and $R_4$ are each independently selected from the group consisting of —H and —C₁.

In some preferred embodiments of the invention, $R_1$ is at the meta-position of —$SO_2$—; $R_1$ is —$OCF_3$ or —$NO_2$; and, $R_2$, $R_3$ and $R_4$ are each independently selected from the group consisting of —H and —C₁.

In some preferred embodiments of the invention, $R_1$ is at the meta-position of —$SO_2$—; $R_1$ is —$OCH_3$, —F, —$NHCOCH_3$, —$OCF_3$ or —$NO_2$; $R_2$, $R_3$ and $R_4$ are each independently selected from the group consisting of —H, —C₁ and —$OCF_2H$.

In some preferred embodiments of the invention, Z is —$COOCH_3$.

In some preferred embodiments of the invention, in Ring A, $R_1$ is at the meta- or para-position of —$SO_2$—.

In some preferred embodiments of the invention, $R_1$ is —$NO_2$.

In some preferred embodiments of the invention, in Ring B, Z is at the ortho-position of —NH—.

In some preferred embodiments of the invention, Z is —$COOCH_3$; in Ring A, $R_1$ is at the meta- or para-position of —$SO_2$—; $R_1$ is —$NO_2$; and in Ring B, Z is at the ortho-position of —NH—.

In some preferred embodiments of the invention, the compound is selected from the compounds listed in Table 1.

In some preferred embodiments of the invention, the COL1A1 promoter has a sequence set forth in SEQ ID NO: 1.

In some preferred embodiments of the invention, the cell is a collagen-producing cell, such as a hepatic stellate cell, a hepatic sinusoidal endothelial cell, a biliary epithelial cell, a fibroblast or an osteoblast.

In some preferred embodiments of the invention, the agent is administered in vivo or in vitro. In some preferred embodiments of the invention, the agent is administered to a subject (e.g. a mammal, such as a bovine, an equine, a caprid, a suidae, a canine, a feline, a rodent, or a primate; e.g. a human), to modulate (e.g. inhibit) the activity of COL1A1 promoter in a cell of the subject. In some preferred embodiments of the invention, the agent is administered to an in vitro cell (e.g. a cell line or a cell from a subject), to modulate (e.g. inhibit) the activity of COL1A1 promoter in the in vitro cell.

In an aspect, the present application provides use of a compound of Formula (I) for modulating (e.g. inhibiting) expression level of a gene associated with liver fibrosis in a cell, or for manufacture of an agent for modulating (e.g. inhibiting) expression level of a gene associated with liver fibrosis in a cell;

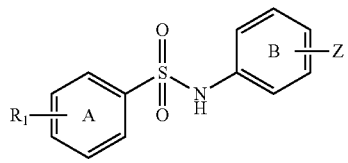

(I)

wherein
$R_1$ is selected from the group consisting of —O—($C_1$-$C_4$alkyl), halogen (e.g. —F, —$C_1$, —Br or —I), —NHCO—($C_1$-$C_4$alkyl), —CONH—($C_1$-$C_4$alkyl), —O-(halo-$C_1$-$C_4$alkyl) and —$NO_2$;
Z is —COO—($C_1$-$C_4$alkyl) or

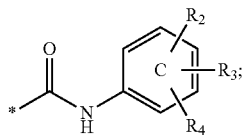

wherein $R_2$, $R_3$ and $R_4$ are each independently selected from the group consisting of —H, —O—($C_1$-$C_4$alkyl), halogen (e.g. —F, —$C_1$, —Br or —I), halo-$C_1$-$C_4$alkyl, —O-(halo-$C_1$-$C_4$alkyl), $C_1$-$C_4$alkyl and —OH.

In some preferred embodiments of the invention, $R_2$, $R_3$ and $R_4$ are not —H simultaneously.

In some preferred embodiments of the invention, in Ring A, $R_1$ is at the ortho-, meta- or para-position of —$SO_2$—.

In some preferred embodiments of the invention, $R_1$ is at the meta- or para-position of —$SO_2$—.

In some preferred embodiments of the invention, $R_1$ is at the meta-position of —$SO_2$—.

In some preferred embodiments of the invention, $R_1$ is selected from the group consisting of —$OCH_3$, —$OCH_2CH_3$, halogen (e.g. —F, —$C_1$, —Br or —I), —$NHCOCH_3$, —$NHCOCH_2CH_3$, —$CONHCH_3$, —$CONHCH_2CH_3$, —$OCF_3$ and —$NO_2$.

In some preferred embodiments of the invention, $R_1$ is selected from the group consisting of —$OCH_3$, —F, —$C_1$, —$NHCOCH_3$, —$CONHCH_3$, —$OCF_3$ and —$NO_2$.

In some preferred embodiments of the invention, $R_1$ is selected from the group consisting of —$OCH_3$, —F, —$NHCOCH_3$, —$OCF_3$ and —$NO_2$.

In some preferred embodiments of the invention, $R_1$ is —$OCF_3$ or —$NO_2$.

In some preferred embodiments of the invention, in Ring B, Z is at the ortho-, meta- or para-position of —NH—.

In some preferred embodiments of the invention, Z is at the ortho- or meta-position of —NH—.

In some preferred embodiments of the invention, Z is at the ortho-position of —NH—.

In some preferred embodiments of the invention, Z is

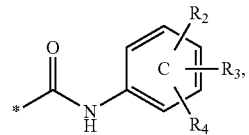

wherein $R_2$, $R_3$ and $R_4$ are each independently selected from the group consisting of —H, —$OCH_3$, —$OCH_2CH_3$, halogen (e.g. —F, —$C_1$, —Br or —I), halo-$C_1$-$C_2$alkyl, —O-(halo-$C_1$-$C_2$alkyl), —$CH_3$, —$CH_2CH_3$ and —OH.

In some preferred embodiments of the invention, $R_2$, $R_3$ and $R_4$ are each independently selected from the group consisting of —H, —$OCH_3$, —$OCH_2CH_3$, halogen (e.g. —F, —$C_1$, —Br or —I), fluoro-$C_1$-$C_2$alkyl, —O-(fluoro-$C_1$-$C_2$alkyl), —$CH_3$, —$CH_2CH_3$ and —OH.

In some preferred embodiments of the invention, $R_2$, $R_3$ and $R_4$ are each independently selected from the group consisting of —H, —$OCH_3$, —F, —$C_1$, —$CF_3$, —$OCF_3$, —$OCF_2H$ and —$CH_3$.

In some preferred embodiments of the invention, $R_2$, $R_3$ and $R_4$ are each independently selected from the group consisting of —H, —F, —$C_1$, —$CF_3$, —$OCF_3$, —$OCF_2H$ and —$CH_3$.

In some preferred embodiments of the invention, $R_2$, $R_3$ and $R_4$ are each independently selected from the group consisting of —H, —F, —$C_1$ and —$OCF_2H$.

In some preferred embodiments of the invention, $R_2$, $R_3$ and $R_4$ are each independently selected from the group consisting of —H and —$C_1$.

In some preferred embodiments of the invention, the compound has a structure of Formula (II):

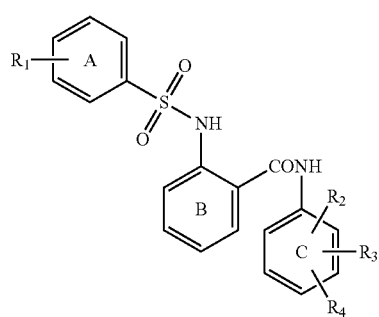

(II)

wherein
$R_1$ is at the meta- or para-position of —$SO_2$—;
$R_1$ is —$OCH_3$, —F, —$NHCOCH_3$, —$OCF_3$ or —$NO_2$;
$R_2$, $R_3$ and $R_4$ are each independently selected from the group consisting of —H, —F, —$C_1$ and —$OCF_2H$, and, $R_2$, $R_3$ and $R_4$ are not —H simultaneously.

In some preferred embodiments of the invention, $R_1$ is at the meta-position of —$SO_2$—.

In some preferred embodiments of the invention, $R_1$ is —$OCF_3$ or —$NO_2$.

In some preferred embodiments of the invention, $R_2$, $R_3$ and $R_4$ are each independently selected from the group consisting of —H and —$C_1$.

In some preferred embodiments of the invention, $R_1$ is at the meta-position of —$SO_2$—; $R_1$ is —$OCF_3$ or —$NO_2$; and, $R_2$, $R_3$ and $R_4$ are each independently selected from the group consisting of —H and —$C_1$.

In some preferred embodiments of the invention, $R_1$ is at the meta-position of —$SO_2$—; $R_1$ is —$OCH_3$, —F, —$NHCOCH_3$, —$OCF_3$ or —$NO_2$; $R_2$, $R_3$ and $R_4$ are each independently selected from the group consisting of —H, —$C_1$ and —$OCF_2H$.

In some preferred embodiments of the invention, Z is —$COOCH_3$.

In some preferred embodiments of the invention, in Ring A, $R_1$ is at the meta- or para-position of —$SO_2$—.

In some preferred embodiments of the invention, $R_1$ is —$NO_2$.

In some preferred embodiments of the invention, in Ring B, Z is at the ortho-position of —NH—.

In some preferred embodiments of the invention, Z is —$COOCH_3$; in Ring A, $R_1$ is at the meta- or para-position of —$SO_2$—; $R_1$ is —$NO_2$; and in Ring B, Z is at the ortho-position of —NH—.

In some preferred embodiments of the invention, the compound is selected from the compounds listed in Table 1.

In some preferred embodiments of the invention, the expression level of a gene associated with liver fibrosis is the level of mRNA transcribed by the gene associated with liver fibrosis.

In some preferred embodiments of the invention, the expression level of a gene associated with liver fibrosis is the level of protein encoded by the gene associated with liver fibrosis.

In some preferred embodiments of the invention, the gene associated with liver fibrosis is selected from the group consisting of COL1A1 gene, TGF-β1 gene, MMP2 gene, α-SMA gene, TIMP1 gene, TIMP2 gene, SPP1 gene and any combination thereof.

In some preferred embodiments of the invention, the agent is administered in vivo or in vitro. In some preferred embodiments of the invention, the agent is administered to a subject (e.g. a mammal, such as a bovine, an equine, a caprid, a suidae, a canine, a feline, a rodent or a primate; e.g. a human), to modulate (e.g. inhibit) expression level of a gene associated with liver fibrosis in a cell of the subject. In some preferred embodiments of the invention, the agent is administered to an in vitro cell (e.g. a cell line or a cell from a subject), to modulate (e.g. inhibit) expression level of a gene associated with liver fibrosis in the in vitro cell.

In an aspect, the present application provides a method for inhibiting liver fibrosis, or preventing and/or treating a liver injury, or improving a liver function, or preventing and/or treating a liver disease associated with liver fibrosis in a subject, comprising administering an effective amount of a compound of Formula (I) to a subject in need thereof;

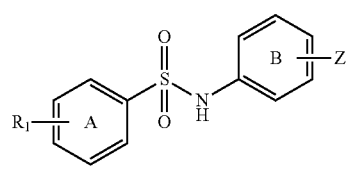

(I)

wherein $R_1$ is selected from the group consisting of —O—($C_1$-$C_4$alkyl), halogen (e.g. —F, —$C_1$, —Br or —I), —NHCO—($C_1$-$C_4$alkyl), —CONH—($C_1$-$C_4$alkyl), —O-(halo-$C_1$-$C_4$alkyl) and —$NO_2$;

Z is —COO—($C_1$-$C_4$alkyl) or

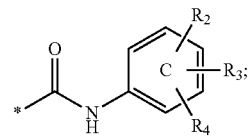

wherein $R_2$, $R_3$ and $R_4$ are each independently selected from the group consisting of —H, —O—($C_1$-$C_4$alkyl), halogen (e.g. —F, —$C_1$, —Br or —I), halo-$C_1$-$C_4$alkyl, —O-(halo-$C_1$-$C_4$alkyl), $C_1$-$C_4$alkyl and —OH.

In some preferred embodiments of the invention, $R_2$, $R_3$ and $R_4$ are not —H simultaneously.

In some preferred embodiments of the invention, in Ring A, $R_1$ is at the ortho-, meta- or para-position of —$SO_2$—.

In some preferred embodiments of the invention, $R_1$ is at the meta- or para-position of —$SO_2$—.

In some preferred embodiments of the invention, $R_1$ is at the meta-position of —$SO_2$—.

In some preferred embodiments of the invention, $R_1$ is selected from the group consisting of —$OCH_3$, —$OCH_2CH_3$, halogen (e.g. —F, —$C_1$, —Br or —I), —$NHCOCH_3$, —$NHCOCH_2CH_3$, —$CONHCH_3$, —$CONHCH_2CH_3$, —$OCF_3$ and —$NO_2$.

In some preferred embodiments of the invention, $R_1$ is selected from the group consisting of —$OCH_3$, —F, —$C_1$, —$NHCOCH_3$, —$CONHCH_3$, —$OCF_3$ and —$NO_2$.

In some preferred embodiments of the invention, $R_1$ is selected from the group consisting of —$OCH_3$, —F, —$NHCOCH_3$, —$OCF_3$ and —$NO_2$.

In some preferred embodiments of the invention, $R_1$ is —$OCF_3$ or —$NO_2$.

In some preferred embodiments of the invention, in Ring B, Z is at the ortho-, meta- or para-position of —NH—.

In some preferred embodiments of the invention, Z is at the ortho- or meta-position of —NH—.

In some preferred embodiments of the invention, Z is at the ortho-position of —NH—.

In some preferred embodiments of the invention, Z is

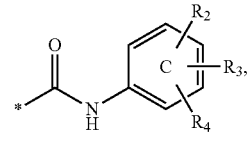

wherein $R_2$, $R_3$ and $R_4$ are each independently selected from the group consisting of —H, —$OCH_3$, —$OCH_2CH_3$, halogen (e.g. —F, —$C_1$, —Br or —I), halo-$C_1$-$C_2$alkyl, —O-(halo-$C_1$-$C_2$alkyl), —$CH_3$, —$CH_2CH_3$ and —OH.

In some preferred embodiments of the invention, $R_2$, $R_3$ and $R_4$ are each independently selected from the group consisting of —H, —$OCH_3$, —$OCH_2CH_3$, halogen (e.g. —F, —$C_1$, —Br or —I), fluoro-$C_1$-$C_2$alkyl, —O-(fluoro-$C_1$-$C_2$alkyl), —$CH_3$, —$CH_2CH_3$ and —OH.

In some preferred embodiments of the invention, $R_2$, $R_3$ and $R_4$ are each independently selected from the group consisting of —H, —$OCH_3$, —F, —$C_1$, —$CF_3$, —$OCF_3$, —$OCF_2H$ and —$CH_3$.

In some preferred embodiments of the invention, $R_2$, $R_3$ and $R_4$ are each independently selected from the group consisting of —H, —F, —$C_1$, —$CF_3$, —$OCF_3$, —$OCF_2H$ and —$CH_3$.

In some preferred embodiments of the invention, $R_2$, $R_3$ and $R_4$ are each independently selected from the group consisting of —H, —F, —$C_1$ and —$OCF_2H$.

In some preferred embodiments of the invention, $R_2$, $R_3$ and $R_4$ are each independently selected from the group consisting of —H and —$C_1$.

In some preferred embodiments of the invention, the compound has a structure of Formula (II):

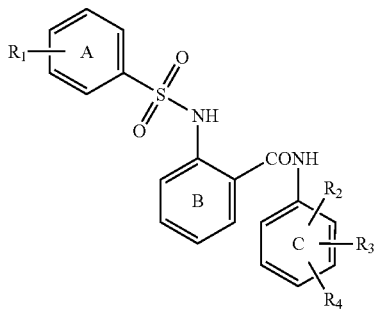

wherein $R_1$ is at the meta- or para-position of —$SO_2$—;

$R_1$ is —$OCH_3$, —F, —$NHCOCH_3$, —$OCF_3$ or —$NO_2$;

$R_2$, $R_3$ and $R_4$ are each independently selected from the group consisting of —H, —F, —$C_1$ and —$OCF_2H$, and, $R_2$, $R_3$ and $R_4$ are not —H simultaneously.

In some preferred embodiments of the invention, $R_1$ is at the meta-position of —$SO_2$—.

In some preferred embodiments of the invention, $R_1$ is —$OCF_3$ or —$NO_2$.

In some preferred embodiments of the invention, $R_2$, $R_3$ and $R_4$ are each independently selected from the group consisting of —H and —$C_1$.

In some preferred embodiments of the invention, $R_1$ is at the meta-position of —$SO_2$—; $R_1$ is —$OCF_3$ or —$NO_2$; and, $R_2$, $R_3$ and $R_4$ are each independently selected from the group consisting of —H and —$C_1$.

In some preferred embodiments of the invention, $R_1$ is at the meta-position of —$SO_2$—; $R_1$ is —$OCH_3$, —F, —$NHCOCH_3$, —$OCF_3$ or —$NO_2$; $R_2$, $R_3$ and $R_4$ are each independently selected from the group consisting of —H, —$C_1$ and —$OCF_2H$.

In some preferred embodiments of the invention, Z is —$COOCH_3$.

In some preferred embodiments of the invention, in Ring A, $R_1$ is at the meta- or para-position of —$SO_2$—.

In some preferred embodiments of the invention, $R_1$ is —$NO_2$.

In some preferred embodiments of the invention, in Ring B, Z is at the ortho-position of —NH—.

In some preferred embodiments of the invention, Z is —$COOCH_3$; in Ring A, $R_1$ is at the meta- or para-position of —$SO_2$—; $R_1$ is —$NO_2$; and in Ring B, Z is at the ortho-position of —NH—.

In some preferred embodiments of the invention, the compound is selected from the compounds listed in Table 1.

In some preferred embodiments of the invention, the liver fibrosis is caused by a liver injury.

In some preferred embodiments of the invention, the liver injury is an acute liver injury or a chronic liver injury.

In some preferred embodiments of the invention, the liver injury is selected from the group consisting of a violence-caused liver injury (e.g. an open liver injury, a closed liver injury), a drug-induced liver injury, a toxic liver injury and a pathological liver injury (e.g. a liver injury caused by viral hepatitis, liver cancer or an autoimmune disease).

In some preferred embodiments of the invention, the liver disease associated with liver fibrosis is selected from the group consisting of: viral hepatitis (e.g. Hepatitis A, Hepatitis B, Hepatitis C, Hepatitis D, Hepatitis E), fatty liver, an autoimmune liver disease, a drug-induced liver disease, toxic hepatopathy and liver cancer.

In some preferred embodiments of the invention, the subject is a mammal, such as a bovine, an equine, a caprid, a suidae, a canine, a feline, a rodent or a primate; preferably, the subject is a human.

In some preferred embodiments of the invention, the compound may be administered to a subject in need thereof by any suitable route, such as orally, parenterally, rectally, intrapulmonarily or topically.

In some preferred embodiments of the invention, the compound is administered in a therapeutically and/or prophylactically effective amount to a subject. In some preferred embodiments of the invention, the administration dose of the compound can be adjusted depending on factors such as pathogenic condition, age, body weight, and gender of a patient or subject, administration route and course of treatment.

In an aspect, the present application provides a method for modulating (e.g. reducing) the content of collagen (e.g. type I collagen) in liver tissue of a subject, comprising administering an effective amount of a compound of Formula (I) to a subject in need thereof;

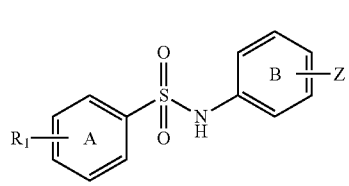

wherein $R_1$ is selected from the group consisting of —O—($C_1$-$C_4$alkyl), halogen (e.g. —F, —$C_1$, —Br or —I), —NHCO—($C_1$-$C_4$alkyl), —CONH—($C_1$-$C_4$alkyl), —O-(halo-$C_1$-$C_4$alkyl) and —$NO_2$;

Z is —COO—($C_1$-$C_4$alkyl) or

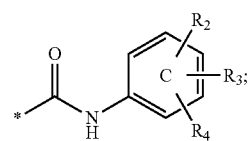

wherein $R_2$, $R_3$ and $R_4$ are each independently selected from the group consisting of —H, —O—($C_1$-$C_4$alkyl), halogen (e.g. —F, —$C_1$, —Br or —I), halo-$C_1$-$C_4$alkyl, $C_1$-$C_4$alkyl and —OH;

In some preferred embodiments of the invention, $R_2$, $R_3$ and $R_4$ are not —H simultaneously.

In some preferred embodiments of the invention, in Ring A, $R_1$ is at the ortho-, meta- or para-position of —$SO_2$—.

In some preferred embodiments of the invention, $R_1$ is at the meta- or para-position of —$SO_2$—.

In some preferred embodiments of the invention, $R_1$ is at the meta-position of —$SO_2$—.

In some preferred embodiments of the invention, $R_1$ is selected from the group consisting of —$OCH_3$, —$OCH_2CH_3$, halogen (e.g. —F, —$C_1$, —Br or —I), —$NHCOCH_3$, —$NHCOCH_2CH_3$, —$CONHCH_3$, —$CONHCH_2CH_3$, —$OCF_3$ and —$NO_2$.

In some preferred embodiments of the invention, $R_1$ is selected from the group consisting of —$OCH_3$, —F, —$C_1$, —$NHCOCH_3$, —$CONHCH_3$, —$OCF_3$ and —$NO_2$.

In some preferred embodiments of the invention, $R_1$ is selected from the group consisting of —$OCH_3$, —F, —$NHCOCH_3$, —$OCF_3$ and —$NO_2$.

In some preferred embodiments of the invention, $R_1$ is —$OCF_3$ or —$NO_2$.

In some preferred embodiments of the invention, in Ring B, Z is at the ortho-, meta- or para-position of —NH—.

In some preferred embodiments of the invention, Z is at the ortho- or meta-position of —NH—.

In some preferred embodiments of the invention, Z is at the ortho-position of —NH—.

In some preferred embodiments of the invention, Z is

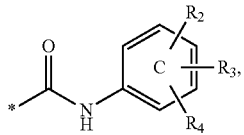

wherein $R_2$, $R_3$ and $R_4$ are each independently selected from the group consisting of —H, —$OCH_3$, —$OCH_2CH_3$, halogen (e.g. —F, —$C_1$, —Br or —I), halo-$C_1$-$C_2$alkyl, —O-(halo-$C_1$-$C_2$alkyl), —$CH_3$, —$CH_2CH_3$ and —OH.

In some preferred embodiments of the invention, $R_2$, $R_3$ and $R_4$ are each independently selected from the group consisting of —H, —$OCH_3$, —$OCH_2CH_3$, halogen (e.g. —F, —$C_1$, —Br or —I), fluoro-$C_1$-$C_2$alkyl, —O-(fluoro-$C_1$-$C_2$alkyl), —$CH_3$, —$CH_2CH_3$ and —OH.

In some preferred embodiments of the invention, $R_2$, $R_3$ and $R_4$ are each independently selected from the group consisting of —H, —$OCH_3$, —F, —$C_1$, —$CF_3$, —$OCF_3$, —$OCF_2H$ and —$CH_3$.

In some preferred embodiments of the invention, $R_2$, $R_3$ and $R_4$ are each independently selected from the group consisting of —H, —F, —$C_1$, —$CF_3$, —$OCF_3$, —$OCF_2H$ and —$CH_3$.

In some preferred embodiments of the invention, $R_2$, $R_3$ and $R_4$ are each independently selected from the group consisting of —H, —F, —$C_1$ and —$OCF_2H$.

In some preferred embodiments of the invention, $R_2$, $R_3$ and $R_4$ are each independently selected from the group consisting of —H and —$C_1$.

In some preferred embodiments of the invention, the compound has a structure of Formula (II):

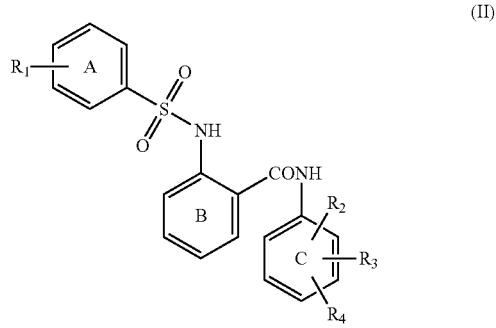

wherein $R_1$ is at the meta- or para-position of —$SO_2$—;

$R_1$ is —$OCH_3$, —F, —$NHCOCH_3$, —$OCF_3$ or —$NO_2$.

$R_2$, $R_3$ and $R_4$ are each independently selected from the group consisting of —H, —F, —$C_1$ and —$OCF_2H$, and, $R_2$, $R_3$ and $R_4$ are not —H simultaneously.

In some preferred embodiments of the invention, $R_1$ is at the meta-position of —$SO_2$—.

In some preferred embodiments of the invention, $R_1$ is —$OCF_3$ or —$NO_2$.

In some preferred embodiments of the invention, $R_2$, $R_3$ and $R_4$ are each independently selected from the group consisting of —H and —$C_1$.

In some preferred embodiments of the invention, $R_1$ is at the meta-position of —$SO_2$—; $R_1$ is —$OCF_3$ or —$NO_2$; and, $R_2$, $R_3$ and $R_4$ are each independently selected from the group consisting of —H and —$C_1$.

In some preferred embodiments of the invention, $R_1$ is at the meta-position of —$SO_2$—;

$R_1$ is —$OCH_3$, —F, —$NHCOCH_3$, —$OCF_3$ or —$NO_2$; $R_2$, $R_3$ and $R_4$ are each independently selected from the group consisting of —H, —$C_1$ and —$OCF_2H$.

In some preferred embodiments of the invention, Z is —$COOCH_3$.

In some preferred embodiments of the invention, in Ring A, $R_1$ is at the meta- or para-position of —$SO_2$—.

In some preferred embodiments of the invention, $R_1$ is —$NO_2$.

In some preferred embodiments of the invention, in Ring B, Z is at the ortho-position of —NH—.

In some preferred embodiments of the invention, Z is —$COOCH_3$; in Ring A, $R_1$ is at the meta- or para-position of —$SO_2$—; $R_1$ is —$NO_2$; and in Ring B, Z is at the ortho-position of —NH—.

In some preferred embodiments of the invention, the compound is selected from the compounds listed in Table 1.

In an aspect, the present application provides a method for modulating (e.g. inhibiting) the activity of COL1A1 promoter in a cell, comprising administering an effective amount of a compound of Formula (I) to a cell in need thereof;

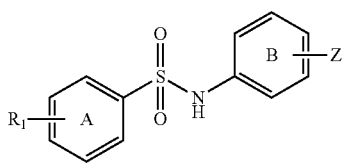

wherein

R₁ is selected from the group consisting of —O—($C_1$-$C_4$alkyl), halogen (e.g. —F, —$C_1$, —Br or —I), —NHCO—($C_1$-$C_4$alkyl), —CONH—($C_1$-$C_4$alkyl), —O-(halo-$C_1$-$C_4$alkyl) and —NO₂;

Z is —COO—($C_1$-$C_4$alkyl) or

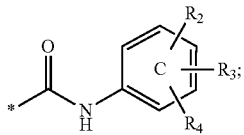

wherein $R_2$, $R_3$ and $R_4$ are each independently selected from the group consisting of —H, —O—($C_1$-$C_4$alkyl), halogen (e.g. —F, —$C_1$, —Br or —I), halo-$C_1$-$C_4$alkyl, —O-(halo-$C_1$-$C_4$alkyl), $C_1$-$C_4$alkyl and —OH.

In some preferred embodiments of the invention, $R_2$, $R_3$ and $R_4$ are not —H simultaneously.

In some preferred embodiments of the invention, in Ring A, $R_1$ is at the ortho-, meta- or para-position of —SO₂—.

In some preferred embodiments of the invention, $R_1$ is at the meta- or para-position of —SO₂—.

In some preferred embodiments of the invention, $R_1$ is at the meta-position of —SO₂—.

In some preferred embodiments of the invention, $R_1$ is selected from the group consisting of —OCH₃, —OCH₂CH₃, halogen (e.g. —F, —$C_1$, —Br or —I), —NHCOCH₃, —NHCOCH₂CH₃, —CONHCH₃, —CONHCH₂CH₃, —OCF₃ and —NO₂.

In some preferred embodiments of the invention, $R_1$ is selected from the group consisting of —OCH₃, —F, —$C_1$, —NHCOCH₃, —CONHCH₃, —OCF₃ and —NO₂.

In some preferred embodiments of the invention, $R_1$ is selected from the group consisting of —OCH₃, —F, —NHCOCH₃, —OCF₃ and —NO₂.

In some preferred embodiments of the invention, $R_1$ is —OCF₃ or —NO₂.

In some preferred embodiments of the invention, in Ring B, Z is at the ortho-, meta- or para-position of —NH—.

In some preferred embodiments of the invention, Z is at the ortho- or meta-position of —NH—.

In some preferred embodiments of the invention, Z is at the ortho-position of —NH—.

In some preferred embodiments of the invention, Z is

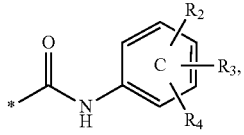

wherein $R_2$, $R_3$ and $R_4$ are each independently selected from the group consisting of —H, —OCH₃, —OCH₂CH₃, halogen (e.g. —F, —$C_1$, —Br or —I), halo-$C_1$-$C_2$alkyl, —O-(halo-$C_1$-$C_2$alkyl), —CH₃, —CH₂CH₃ and —OH.

In some preferred embodiments of the invention, $R_2$, $R_3$ and $R_4$ are each independently selected from the group consisting of —H, —OCH₃, —OCH₂CH₃, halogen (e.g. —F, —$C_1$, —Br or —I), fluoro-$C_1$-$C_2$alkyl, —O-(fluoro-$C_1$-$C_2$alkyl), —CH₃, —CH₂CH₃ and —OH.

In some preferred embodiments of the invention, $R_2$, $R_3$ and $R_4$ are each independently selected from the group consisting of —H, —OCH₃, —F, —$C_1$, —CF₃, —OCF₃, —OCF₂H and —CH₃.

In some preferred embodiments of the invention, $R_2$, $R_3$ and $R_4$ are each independently selected from the group consisting of —H, —F, —$C_1$, —CF₃, —OCF₃, —OCF₂H and —CH₃.

In some preferred embodiments of the invention, $R_2$, $R_3$ and $R_4$ are each independently selected from the group consisting of —H, —F, —$C_1$ and —OCF₂H.

In some preferred embodiments of the invention, $R_2$, $R_3$ and $R_4$ are each independently selected from the group consisting of —H and —$C_1$.

In some preferred embodiments of the invention, the compound has a structure of Formula (II):

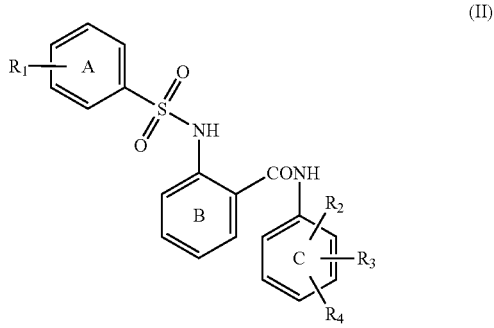

wherein $R_1$ is at the meta- or para-position of —SO₂—;

$R_1$ is —OCH₃, —F, —NHCOCH₃, —OCF₃ or —NO₂;

$R_2$, $R_3$ and $R_4$ are each independently selected from the group consisting of —H, —F, —$C_1$ and —OCF₂H, and, $R_2$, $R_3$ and $R_4$ are not —H simultaneously.

In some preferred embodiments of the invention, $R_1$ is at the meta-position of —SO₂—.

In some preferred embodiments of the invention, $R_1$ is —OCF₃ or —NO₂.

In some preferred embodiments of the invention, $R_2$, $R_3$ and $R_4$ are each independently selected from the group consisting of —H and —$C_1$.

In some preferred embodiments of the invention, $R_1$ is at the meta-position of —SO₂—; $R_1$ is —OCF₃ or —NO₂; and, $R_2$, $R_3$ and $R_4$ are each independently selected from the group consisting of —H and —$C_1$.

In some preferred embodiments of the invention, $R_1$ is at the meta-position of —SO₂—; $R_1$ is —OCH₃, —F, —NHCOCH₃, —OCF₃ or —NO₂; $R_2$, $R_3$ and $R_4$ are each independently selected from the group consisting of —H, —$C_1$ and —OCF₂H.

In some preferred embodiments of the invention, Z is —COOCH₃.

In some preferred embodiments of the invention, in Ring A, $R_1$ is at the meta- or para-position of —SO₂—.

In some preferred embodiments of the invention, $R_1$ is —NO₂.

In some preferred embodiments of the invention, in Ring B, Z is at the ortho-position of —NH—.

In some preferred embodiments of the invention, Z is —COOCH$_3$; in Ring A, R$_1$ is at the meta- or para-position of —SO$_2$—; R$_1$ is —NO$_2$; and in Ring B, Z is at the ortho-position of —NH—.

In some preferred embodiments of the invention, the compound is selected from the compounds listed in Table 1.

In some preferred embodiments of the invention, the COL1A1 promoter has a sequence set forth in SEQ ID NO: 1.

In some preferred embodiments of the invention, the cell is a collagen-producing cell, such as a hepatic stellate cell, a hepatic sinusoidal endothelial cell, a biliary epithelial cell, a fibroblast or an osteoblast.

In some preferred embodiments of the invention, the compound is administered in vivo or in vitro. In some preferred embodiments of the invention, the compound is administered to a subject (a bovine, an equine, a caprid, a suidae, a canine, a feline, a rodent or a primate; e.g. a human), to modulate (e.g. inhibit) the activity of COL1A1 promoter in a cell of the subject. In some preferred embodiments of the invention, the compound is administered to an in vitro cell (e.g. a cell line or a cell from a subject), to modulate (e.g. inhibit) the activity of COL1A1 promoter in the in vitro cell.

In an aspect, the present application provides a method for modulating (e.g. inhibiting) expression level of a gene associated with liver fibrosis in a cell, comprising administering an effective amount of a compound of Formula (I) to a cell in need thereof;

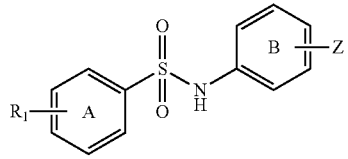
(I)

wherein
R$_1$ is selected from the group consisting of —O—(C$_1$-C$_4$alkyl), halogen (e.g. —F, —C$_1$, —Br or —I), —NHCO—(C$_1$-C$_4$alkyl), —CONH—(C$_1$-C$_4$alkyl), —O-(halo-C$_1$-C$_4$alkyl) and —NO$_2$;
Z is —COO—(C$_1$-C$_4$alkyl) or

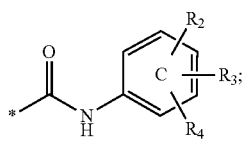

wherein R$_2$, R$_3$ and R$_4$ are each independently selected from the group consisting of —H, —O—(C$_1$-C$_4$alkyl), halogen (e.g. —F, —C$_1$, —Br or —I), halo-C$_1$-C$_4$alkyl, —O-(halo-C$_1$-C$_4$alkyl), C$_1$-C$_4$alkyl and —OH.

In some preferred embodiments of the invention, R$_2$, R$_3$ and R$_4$ are not —H simultaneously.

In some preferred embodiments of the invention, in Ring A, R$_1$ is at the ortho-, meta- or para-position of —SO$_2$—.

In some preferred embodiments of the invention, R$_1$ is at the meta- or para-position of —SO$_2$—.

In some preferred embodiments of the invention, R$_1$ is at the meta-position of —SO$_2$—.

In some preferred embodiments of the invention, R$_1$ is selected from the group consisting of —OCH$_3$, —OCH$_2$CH$_3$, halogen (e.g. —F, —C$_1$, —Br or —I), —NHCOCH$_3$, —NHCOCH$_2$CH$_3$, —CONHCH$_3$, —CONHCH$_2$CH$_3$, —OCF$_3$ and —NO$_2$.

In some preferred embodiments of the invention, R$_1$ is selected from the group consisting of —OCH$_3$, —F, —C$_1$, —NHCOCH$_3$, —CONHCH$_3$, —OCF$_3$ and —NO$_2$.

In some preferred embodiments of the invention, R$_1$ is selected from the group consisting of —OCH$_3$, —F, —NHCOCH$_3$, —OCF$_3$ and —NO$_2$.

In some preferred embodiments of the invention, R$_1$ is —OCF$_3$ or —NO$_2$.

In some preferred embodiments of the invention, in Ring B, Z is at the ortho-, meta- or para-position of —NH—.

In some preferred embodiments of the invention, Z is at the ortho- or meta-position of —NH—.

In some preferred embodiments of the invention, Z is at the ortho-position of —NH—.

In some preferred embodiments of the invention, Z is

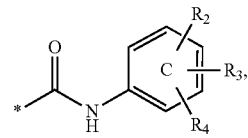

wherein R$_2$, R$_3$ and R$_4$ are each independently selected from the group consisting of —H, —OCH$_3$, —OCH$_2$CH$_3$, halogen (e.g. —F, —C$_1$, —Br or —I), halo-C$_1$-C$_2$alkyl, —O-(halo-C$_1$-C$_2$alkyl), —CH$_3$, —CH$_2$CH$_3$ and —OH.

In some preferred embodiments of the invention, R$_2$, R$_3$ and R$_4$ are each independently selected from the group consisting of —H, —OCH$_3$, —OCH$_2$CH$_3$, halogen (e.g. —F, —C$_1$, —Br or —I), fluoro-C$_1$-C$_2$alkyl, —O-(fluoro-C$_1$-C$_2$alkyl), —CH$_3$, —CH$_2$CH$_3$ and —OH.

In some preferred embodiments of the invention, R$_2$, R$_3$ and R$_4$ are each independently selected from the group consisting of —H, —OCH$_3$, —F, —C$_1$, —CF$_3$, —OCF$_3$, —OCF$_2$H and —CH$_3$.

In some preferred embodiments of the invention, R$_2$, R$_3$ and R$_4$ are each independently selected from the group consisting of —H, —F, —C$_1$, —CF$_3$, —OCF$_3$, —OCF$_2$H and —CH$_3$.

In some preferred embodiments of the invention, R$_2$, R$_3$ and R$_4$ are each independently selected from the group consisting of —H, —F, —C$_1$ and —OCF$_2$H.

In some preferred embodiments of the invention, R$_2$, R$_3$ and R$_4$ are each independently selected from the group consisting of —H and —C$_1$.

In some preferred embodiments of the invention, the compound has a structure of Formula (II):

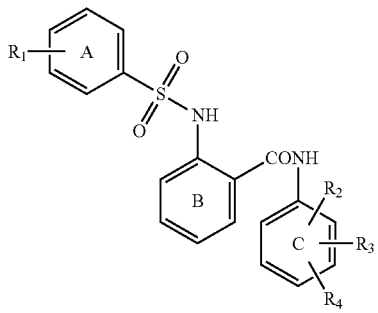

(II)

wherein
R$_1$ is at the meta- or para-position of —SO$_2$—;
R$_1$ is —OCH$_3$, —F, —NHCOCH$_3$, —OCF$_3$ or —NO$_2$;
R$_2$, R$_3$ and R$_4$ are each independently selected from the group consisting of —H, —F, —C$_1$ and —OCF$_2$H, and, R$_2$, R$_3$ and R$_4$ are not —H simultaneously.

In some preferred embodiments of the invention, R$_1$ is at the meta-position of —SO$_2$—.

In some preferred embodiments of the invention, R$_1$ is —OCF$_3$ or —NO$_2$.

In some preferred embodiments of the invention, R$_2$, R$_3$ and R$_4$ are each independently selected from the group consisting of —H and —C$_1$.

In some preferred embodiments of the invention, R$_1$ is at the meta-position of —SO$_2$—; R$_1$ is —OCF$_3$ or —NO$_2$; and, R$_2$, R$_3$ and R$_4$ are each independently selected from the group consisting of —H and —C$_1$.

In some preferred embodiments of the invention, R$_1$ is at the meta-position of —SO$_2$—; R$_1$ is —OCH$_3$, —F, —NHCOCH$_3$, —OCF$_3$ or —NO$_2$; R$_2$, R$_3$ and R$_4$ are each independently selected from the group consisting of —H, —C$_1$ and —OCF$_2$H.

In some preferred embodiments of the invention, Z is —COOCH$_3$.

In some preferred embodiments of the invention, in Ring A, R$_1$ is at the meta- or para-position of —SO$_2$—.

In some preferred embodiments of the invention, R$_1$ is —NO$_2$.

In some preferred embodiments of the invention, in Ring B, Z is at the ortho-position of —NH—.

In some preferred embodiments of the invention, Z is —COOCH$_3$; in Ring A, R$_1$ is at the meta- or para-position of —SO$_2$—; R$_1$ is —NO$_2$; and in Ring B, Z is at the ortho-position of —NH—.

In some preferred embodiments of the invention, the compound is selected from the compounds listed in Table 1.

In some preferred embodiments of the invention, the expression level of a gene associated with liver fibrosis is the level of mRNA transcribed by the gene associated with liver fibrosis.

In some preferred embodiments of the invention, the expression level of a gene associated with liver fibrosis is the level of protein encoded by the gene associated with liver fibrosis.

In some preferred embodiments of the invention, the gene associated with liver fibrosis is selected from the group consisting of COL1A1 gene, TGF-β1 gene, MMP2 gene, α-SMA gene, TIMP1 gene, TIMP2 gene, SPP1 gene and any combination thereof.

In some preferred embodiments of the invention, the cell is a collagen-producing cell, such as a hepatic stellate cell, a hepatic sinusoidal endothelial cell, a biliary epithelial cell, a fibroblast or an osteoblast.

In some preferred embodiments of the invention, the compound is administered in vivo or in vitro. In some preferred embodiments of the invention, the compound is administered to a subject (e.g. a mammal, such as a bovine, an equine, a caprid, a suidae, a canine, a feline, a rodent or a primate; e.g. a human), to modulate (e.g. inhibit) expression level of a gene associated with liver fibrosis in a cell of the subject. In some preferred embodiments of the invention, the compound is administered to an in vitro cell (e.g. a cell line or a cell from a subject), to modulate (e.g. inhibit) expression level of a gene associated with liver fibrosis in the in vitro cell.

Beneficial Effects of the Invention

The inventor of the present application found for the first time that (benzenesulfonamido) benzamide compounds can inhibit the activity of COL1A1 promoter in a cell; such compounds can reduce the content of collagen (e.g. type I collagen) in liver tissue; such compounds can inhibit expression level of a gene associated with liver fibrosis in a cell. Therefore, (benzenesulfonamido) benzamide compounds can be used to inhibit liver fibrosis, prevent and/or treat liver injury, improve liver function, or prevent and/or treat a liver disease associated with liver fibrosis.

The embodiments of the invention are illustrated in detail by reference to the following drawings and examples. However, it is understood by those skilled in the art that the following drawings and examples are used only for the purpose of illustrating the invention, rather than limiting the protection scope of the invention. According to the detailed description of the following drawings and preferred embodiments, various purposes and advantages of the invention are obvious for those skilled in the art.

Figure 1:
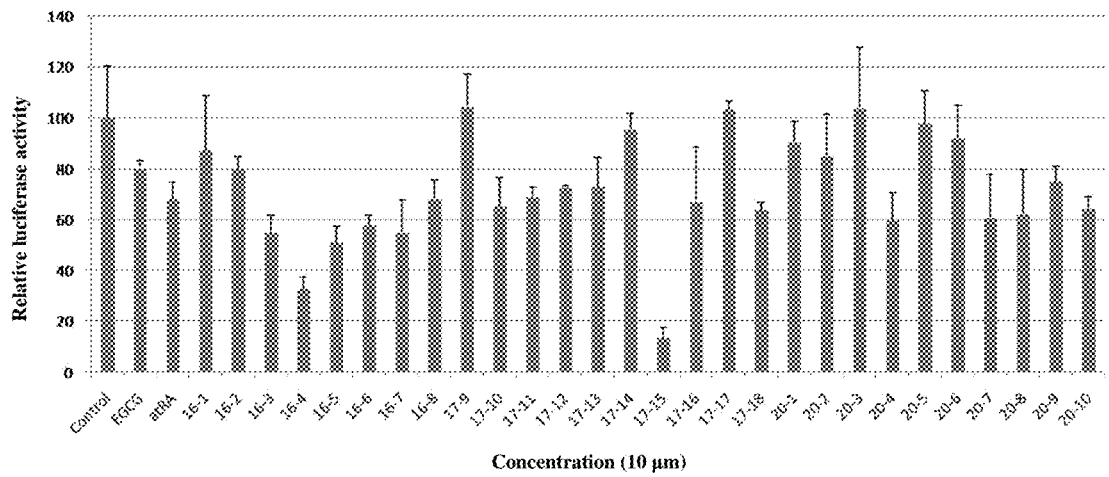
FIG. 1 shows the results on luciferase activity after (benzenesulfonamido) benzamide compounds were applied to LX2-COL cells in Example 1. The results showed that (benzenesulfonamido) benzamide compounds inhibited COL1A1 promoter to different extents.

Information on the sequence involved in the invention is as follows:

| SEQ ID NO: | Description |
|---|---|
| 1 | COL1A1 promoter |

Sequence information

SEQ ID NO: 1: 2436 bp gtgggaaagcctggatgggaaacatatggggaggggcggggagctgcagg caggagcccttcttactacgaaaacccaagaagcaaggaagtggacaggt cactaaccctcatactaccaagccctgcggcaccctgccctagaccacca ctctaaatgtctgttccctccaaaaacaggaccctgtcgcctattaggg aggggttctcttggaactgacccacagtaggggcaggactttggtgggt tcaagaactgccatctcagcacctcagcccctagtcctgccctgcagtc gctggcactaggcgggggcagaccctgggccacaagttgctgccacatgg tcgggataattgatgaaggtccatccctccattgctgtctccagccctgc ctctctggaaactctatatttccctttaattatagcccctgcagtctcc ctctgctgcccacccgcaccgctcatcctggctgcccacggccagccgg ccagccgacgtggctccctcccttctgttccttttttttccccttgcc ttcgttgcacaaaaccagctggggagggcgtggagagggcggggggag gcaatggaatcttggatggtttggggaggcgggactccccgcttccacg tttgcagctctggagcaccggggtggggagctgcacaggagggagagaa atgaacagggcactgcaaggagaccccaggccttctctcagccctacag agtttctcaggacgaggtagattgggttgaggcagagccttgttggggg aatgggacatggaggaagaaggacgtggagttctagagccatcttcctt agatatagcctgctgtccttcgggtcccagacccttcagagtgtacag atgattctctctggttcctaaggcatagagcaatgaccgggattttcaag aaagagatgaggcagtgggaagtagcccctaaaacaaagtcaatcatcct ctgcagcccatcccacaccccaaaggaaagtttcacccagacacccaaa atatcccatacatccccaacactgagtccaggtacaactggagaagggggc tttatgcagctcccagaaagacaccccttagctaagtgccctccctcca cccaggttctctctggttggactgtgctgggaaggagggtctctaagcag cccctggccacagccatggcaaacaaaactcttctctaagtcaccaatga tcacaggcctcccactaaaaatacttcccaactctggggtggaagagttt gggggatgaatttttaggggattgcaagccccaatccccacctctgtgtc -continued

```
cctagaatcccccacccctaccttggctgctccatcacccaaccaccaaa gctttcttctgcagaggccacctagtcatgtttctcaccctgcacctcag cctccccactccatctctcaatcatgcctagggtttggaggaaggcattt gattctgttctggagcacagcagaagaattgacatcctcaaaattaaaac tcccttgcctgcacccctccctcagatatctgattcttaatgtctagaaa ggaatctgtaaattgttccccaaatattcctaagctccatccctagcca caccagaagacaccccaaacaggcacatctttttaattcccagcttcct ctgttttggagaggtcctcagcatgcctctttatgccctcccttagctc ttgccaggatatcagagggtgactggggcacagccaggaggaccccctcc ccaacaccccaaccttccacctttggaagtctccccacccagctcccc agttccccagttccacttcttctagattggaggtcccaggaagagagcag aggggcaccccctacccactggttagcccacgccattctgaggacccagct gcaccccctaccacagcacctctggcccaggctgggctgggggctgggga ggcagagctgcgaagaggggagatgtggggtggactcccttccctcctcc tcccctctccattccaactcccaaattgggggccgggccaggcagctct gattggctggggcacgggcggccggctccccctctccgaggggcagggtt cctcctgctctccatcaggacagtataaaaggggcccgggccagtcgtc ggagcagacgggagtttctcctcggggtcggagcaggaggcacgcggagt gtgaggccacgcatgagcggacgctaaccccctcccagccacaaagagt ctacatgtctagggtctagacatgttcagctttgtggacctccggctcct gctcctcttagcggccaccgccctcctgacgcacggccaagaggaaggcc aagtcgagggccaagacgaagacagtaagtcccaaa
```

SPECIFIC MODES FOR CARRYING OUT THE INVENTION

The embodiments of the invention are illustrated in detail by reference to the following examples. However, it is understood by those skilled in the art that the examples are used only for the purpose of illustrating the invention, rather than limiting the protection scope of the invention. In the case where the concrete conditions are not indicated in the examples, the examples are carried out according to conventional conditions or the conditions recommended by the manufacturer. The agents or instruments of which the manufacturer are not indicated are regular products that can be purchased on the market.

Example 1

In the example, the compounds listed in Table 1 were studied for their inhibitory effects on COL1A1 promoter by a cell screening model using COL1A1 promoter as target. The test compounds were prepared by the method as disclosed in CN patent application CN103183623A.

Experimental Procedure:

By reference to the method in CN patent application CN104232588A, a cell screening model using COL1A1 promoter as target was established, and LX2-COL monoclonal cell line was obtained. After serum-free culture of LX2-COL monoclonal cell line, cytokine TGF-β1 was added for induction, and meanwhile a test compound (10 μM) was added. Epigallocatechin gallate (EGCG) and all-trans-retinoic acid (atRA) were used as positive control drugs. The assay was carried out by using Luciferase Assay Kit, and the results were shown in FIG. 1.

The results showed that the test compounds inhibited COL1A1 promoter to different extents. At the same dose, the test compounds showed better inhibitory effects than the positive control compounds EGCG and atRA. It has been reported definitely that EGCG is a compound capable of inhibiting liver fibrosis; and it has also be demonstrated definitely that all-trans-retinoic acid (atRA) has an improved effect on liver fibrosis and liver cirrhosis, and has been subjected to clinical trial. The results above showed that (benzenesulfonamido) benzamide compounds could inhibit the activity of COL1A1 promoter.

Example 2

In the example, the compounds 16-4, 16-5 and 17-15 were tested for their inhibitory effects on activity of COL1A1 promoter by a dual-luciferase reporter assay system.

Experimental Procedure:

At 37° C., 5% $CO_2$, human hepatic stellate cells LX2 were cultured in DMEM medium containing 10% fetal bovine serum (Gibco). After the cells reached a confluence of about 95%, the cells were spread onto a 96-well plate at $2\times10^4$ cells per well. After the cells reached a confluence of about 90%, the cells were subjected to serum-free culture in DMEM medium (Gibco) containing no fetal bovine serum for 24 h. LX2 cells were co-transfected with pGL4.17-COL1A1 plasmid (constructed by reference to the method in CN patent application CN104232588A) and Renailla plasmid by using Lipo2000, and were induced by TGF-β1 (2 ng/ml) 6 h after transfection; meanwhile, the compounds 16-4, 16-5 and 17-15 were added at a concentration of 1 μmol/L, 5 μmol/L and 10 μmol/L, respectively, wherein at least 3 replicate wells were set for each experiment. The cells were further cultured for 24 h. In accordance with the operations described in the instruction of Dual-Glo™ Luciferase Assay System, the medium was discarded, and the cells were washed with PBS once. Cells were lysed by the addition of 1×PLB (20 μL/well) (within 15 min), luciferase substrate (50 μL/well) was added for assay, and a stop solution (50 μL/well) was added for assay.

Figure 2:
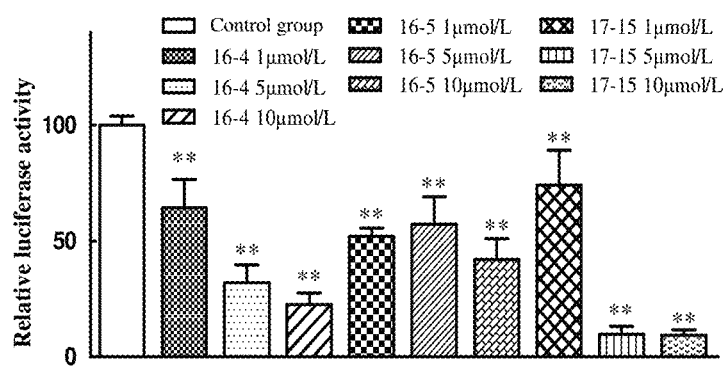
FIG. 2 shows the results on luciferase activity after the compounds 16-4, 16-5 and 17-15 were applied to LX2-COL cells in Example 2. In the figure, **represents p<0.01 compared to control group (administration concentration is 0). The results showed that the compounds 16-4, 16-5 and 17-15 inhibited COL1A1 promoter in a dose-dependent manner.

FIG. 2 showed the results. In the figure, **represents p<0.01 compared to control group (administration concentration is 0). As shown in the figure, with the increase in the concentration of the compounds 16-4, 16-5 and 17-15, the relative luciferase activity reduced significantly. The results showed that the compounds 16-4, 16-5 and 17-15 could inhibit the activity of COL1A1 promoter in a dose-dependent manner.

Example 3

In the example, the compounds 16-4, 16-5, and 17-15 were tested for in vitro activity against liver fibrosis.

1. TGF-β1-Induced LX2 Cells

In DMEM (Gibco) medium containing 10% fetal bovine serum, LX2 cells were cultured at 37° C., 5% $CO_2$. The cells were spread on a 6-well plate at $1\times10^5$ cells per well. After culture for 24 h, the original medium was discarded, the cells were washed with PBS once, and DMEM (Gibco) medium without 10% fetal bovine serum was added. After starvation culture for 24 h, TGF-β1 (2 ng/ml), and the compounds 16-4, 16-5 and 17-15 (at a concentration of 1 μmmol/L, 5 μmmol/L and 10 μmmol/L, respectively) were added, and control group (not induced by TGF-β1) and TGF-β1-induced group (with the addition of TGF-β1 alone) were set. After further culture for 24 h, the samples were taken.

2. Real-Time PCR Assay

In accordance with the TRizol method, the total RNA in LX2 cells were extracted, and in accordance with the operations described in the instruction of Roche Transcriptor First Strand cDNA Synthesis Kit, the total RNA of LX2 was reverse transcribed into cDNA. The cDNA obtained, sterile water, Roche FastStart Universal Probe Master (Rox) and ABI TaqMan probes (COL1A1, TGF-β1, MMP2) were used to prepare a 20 μL reaction system, which was analyzed by ABI 7500 Fast Real-Time PCR System.

Figure 3:
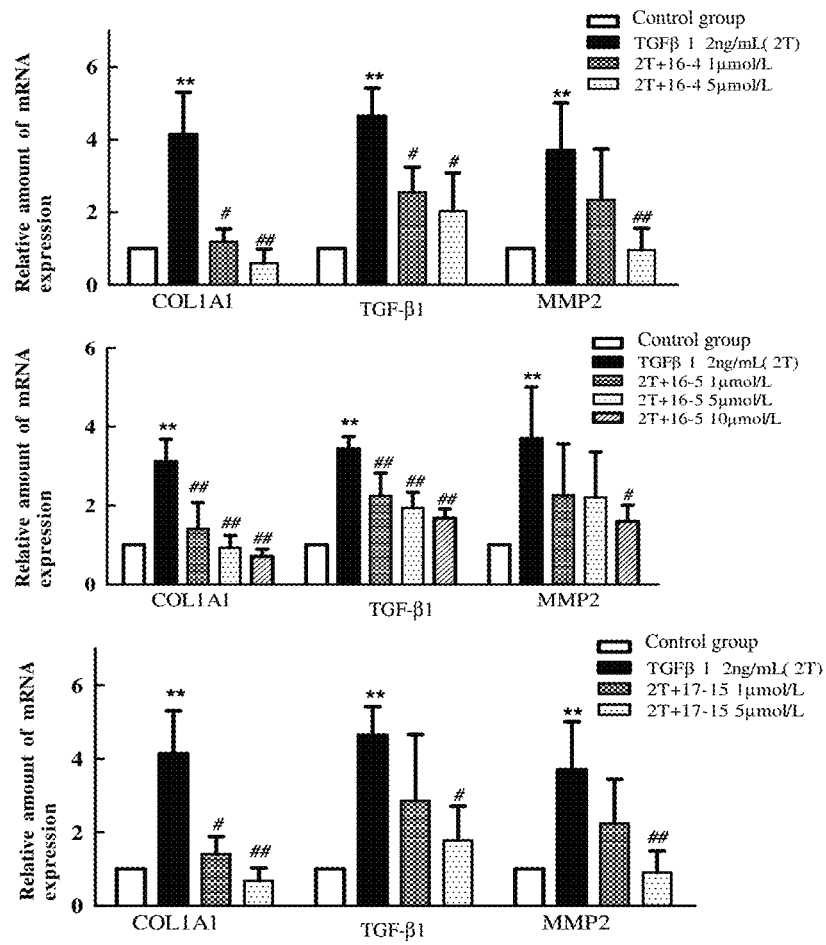
FIG. 3 shows the results on the expression level of mRNA of COL1A1, TGF-β1, and MMP2 determined by real-time PCR assay, after the compounds 16-4, 16-5 and 17-15 were applied to TGF-β1-induced LX2 cells in Example 3. The results showed that the compounds 16-4, 16-5 and 17-15 could significantly inhibit the expression level of mRNA of COL1A1, TGF-β1 and MMP2.

FIG. 3 showed the results. In the figure, *represents $p<0.05$ compared to control group (LX2 cells that are not induced and activated); **represents $p<0.01$ compared to control group (LX2 cells that are not induced and activated); # represents $p<0.05$ compared to TGF-β1-induced group (administration concentration is 0); ## represents $p<0.01$ compared to TGF-β1-induced group (administration concentration is 0). The results showed that the compounds 16-4, 16-5 and 17-15 could significantly inhibit the expression levels of mRNA of COL1A1, TGF-β1 and MMP2.

3. Western Blot Assay

Figure 4:
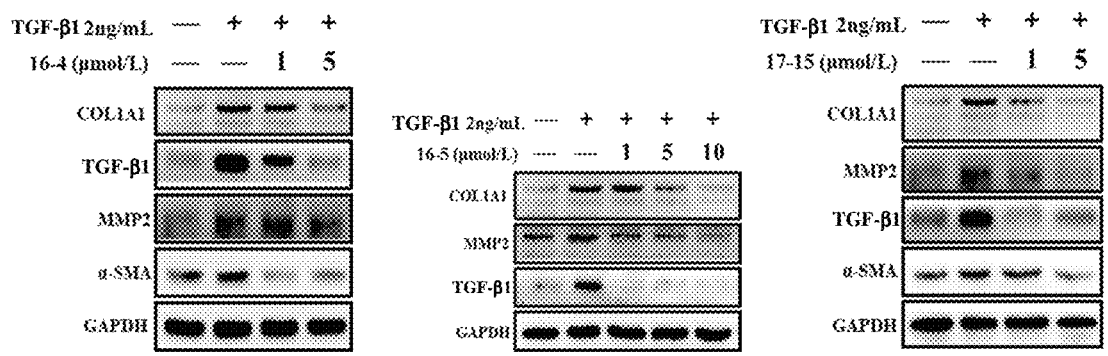
FIG. 4 shows the results on the expression level of COL1A1, TGF-β1, MMP2 and α-SMA protein determined by Western blot assay, after the compounds 16-4, 16-5 and 17-15 were applied to TGF-β1-induced LX2 cells in Example 3. The results showed that the compounds 16-4, 16-5, and 17-15 could significantly inhibit the expression level of COL1A1, TGF-β1, MMP2 and α-SMA protein.

Proteins in LX2 cells were extracted with RAPI lysis solution (containing 1% PMSF), and the protein concentration was determined by BCA method. The sample was loaded at 20 μg/20 μL, subjected to polyacrylamide gel electrophoresis, transferred to a membrane, blocked with 5% skim milk, incubated with a primary antibody, washed with PBST, incubated with a secondary antibody, and imaged with ChemiImager 5500 imaging system. FIG. 4 showed the results. The results showed that the compounds 16-4, 16-5 and 17-15 could significantly inhibit the expression of COL1A1, TGF-β1, MMP2 and α-SMA protein.

Example 4

In the example, the compounds 16-4 and 17-15 were tested for their safety in Kunming mice.

Kunming mice (with a body weight of 18-22 g) were randomly divided into control group, 16-4 administration group, and 17-15 administration group, with 4 mice for each group, administered at a dose of 0 mg/kg, 50 mg/kg, 500 mg/kg, 1000 mg/kg and 2000 mg/kg. At the first day of experiment, drugs were intragastrically administered to 16-4 administration group and 17-15 administration group, and normal saline was administered to control group. The body weight and physical conditions of mice (for example, being short of breath or not, having bleeding spots in skin or not, etc.) and whether mice died or not were recorded every day. After observation for 14 days, the mice were sacrificed.

Figure 5:
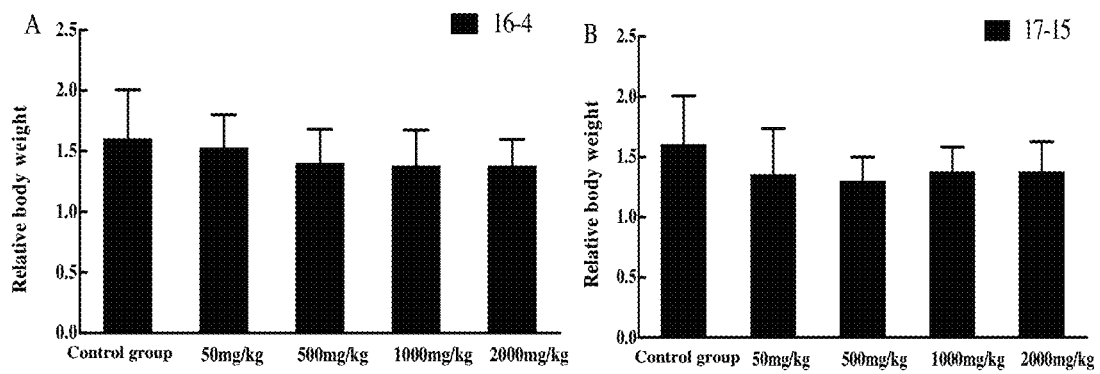
FIG. 5 shows changes in body weight of mice in 16-4 administration group (FIG. 5A) and 17-15 administration group (FIG. 5B) in Example 4, wherein, relative body weight=body weight at Day 14÷body weight at Day 1. The results showed that 14 days after administration, no significant decrease in body weight occurred in these groups of mice, and no signs of intoxication were observed and no death occurred, indicating a relatively high drug safety.
Figure 6:
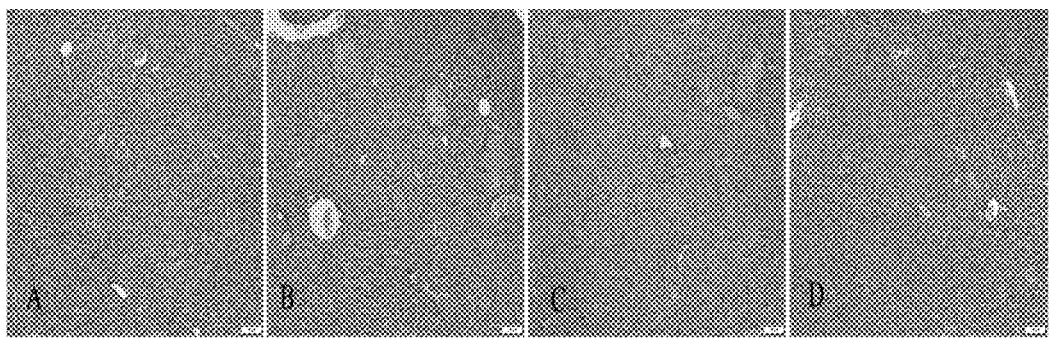
FIG. 6 shows the HE staining results of the liver tissue slices of rats in control group (FIG. 6A), ANIT-induced group (FIG. 6B), 16-4 administration group (FIG. 6C) and 16-5 administration group (FIG. 6D) in Example 5. The results showed that compared to ANIT-induced group, 16-4 administration group and 16-5 administration group had the liver injury improved.

FIGS. 5A and 5B showed changes in the body weight of mice in 16-4 administration group and 17-15 administration group, respectively, wherein relative body weight=body weight at Day 14÷body weight at Day 1. The results showed that 14 days after administration, no significant decrease in body weight occurred in these groups of mice, and no signs of intoxication were observed and no death occurred, indicating a relatively high drug safety.

Example 5

In the example, the compounds 16-4 and 16-5 were tested for their protection against liver injury by using an alpha-naphthylisothiocyanate (ANIT)-induced liver injury model.

Kunming female mice (with a body weight of 22-25 g) were randomly divided into control group, ANIT-induced group, 16-4 (400 mg/kg) administration group, and 16-5 (400 mg/kg) administration group, with 10 mice for each group. Drugs were intragastrically administered to 16-4 administration group and 16-5 administration group for 5 days, and normal saline was administered to control group and ANIT-induced group; after starvation treatment for 12 h, ANIT-induced group, 16-4 administration group and 16-5 administration group were induced with ANIT (75 mg/kg by intragastrical administration), and meanwhile corn oil was intragastrically administered to control group. After further administration for 2 days (i.e. after induction with ANIT for 48 h), liver tissues were harvested, and subjected to pathological section and HE staining.

FIG. 6A-6D showed the HE staining results of the liver tissue slices of rats in control group, ANIT-induced group, 16-4 administration group and 16-5 administration group, respectively. As shown in the figure, compared to ANIT-induced group, 16-4 administration group and 16-5 administration group had the liver injury improved. The results showed that the compound 16-4 and 16-5 had the effect of relieving liver injury, and could be used in the treatment of liver injury.

Example 6

In the example, SD rat bile duct ligation (BDL) model was prepared, to which drugs were administered.

SD male rats (with a body weight of 180-200 g) were randomly divided into sham operation group, BDL model group and 16-4 administration group, wherein sham operation group included 6 rats, BDL model group included 8 rats, and 16-4 administration group included 6 rats. Animals were fasted for 12 hours before surgery. After anesthetization with isoflurane, the abdomen of rat was opened under aseptic conditions, the liver was lifted, the duodenum was pulled aside, and 2-3 cm common bile duct was separate. Ligations were performed twice with silk thread No. 000 at the place proximal to duodenum and the place proximal to porta hepatis, respectively. The common bile duct was cut off at the middle of the two ligation places. After the liver was put back, the cut was sutured. In sham operation group, the abdomen was just opened, and then sutured. After recovery from anesthesia, the animals were subjected to normal diet, with free access to water. 2 days after surgery, the compound 16-4 (100 mg/kg) was intraperitoneally injected to 16-4 administration group, and normal saline was intraperitoneally injected to sham operation group and BDL model group, once a day. After administration for 14 days, samples such as urine, blood, bile, liver, kidney and ileum were collected from the animals after being fasted for 12 hours.

Example 7

In the example, the compound 16-4 was studied for its effect on the liver function of BDL rat.

Blood samples were taken from rats of each group in Example 6, and the rats were fasted for 12 h before taking samples. The rats were anesthetized with 10% chloral hydrate, and blood was collected via aorta ventralis, on standing at room temperature for 1 h, and centrifuged at 3000 rpm for 5 min. The serum was tested for serum biochemical indexes. The results were shown in Table 2. The results showed that the compound 16-4 could reduce the activity of alanine aminotransferase (ALT), alkaline phosphatase (ALP), and γ-glutamyltransferase (γ-GGT), indicating that the compound 16-4 could improve the liver function of BDL rats.

TABLE 2

Effect of the compound 16-4 on serum liver function in BDL model rat

| Serum biochemical indexes | control group (n = 6) | BDL model group (n = 8) | 16-4 group (100 mg/kg) (n = 6) |
|---|---|---|---|
| alanine aminotransferase ALT (U/L) | 33.33 ± 3.78 | 94.70 ± 24.12** | 68.20 ± 11.86# |
| alkaline phosphatase ALP(U/L) | 241.17 ± 66.41 | 476.30 ± 77.19** | 383.60 ± 56.45# |
| γ-glutamyltransferase γ-GGT (U/L) | 0.17 ± 0.41 | 44.90 ± 8.16** | 27.40 ± 10.26# |

**p < 0.01, compared to control group;
p < 0.05, compared to BDL model group.

Example 8

In the example, the compound 16-4 was studied for its effect on pathological structure of BDL rat liver.

The liver tissue samples were taken from rats of each group in Example 6, and the rats were fasted for 12 hours before taking samples. The rats were anesthetized with 10% chloral hydrate and the liver tissue was taken. The hepatic lobar tissue blocks were cut off and fixed in 4% neutral formaldehyde solution. By carrying out the steps such as dehydration, paraffin embedding, slicing and baking, paraffin slices were made. Hematoxylin-eosin (HE) staining solution was used for staining, and changes in pathological structure of rat liver tissue were observed.

Figure 7:
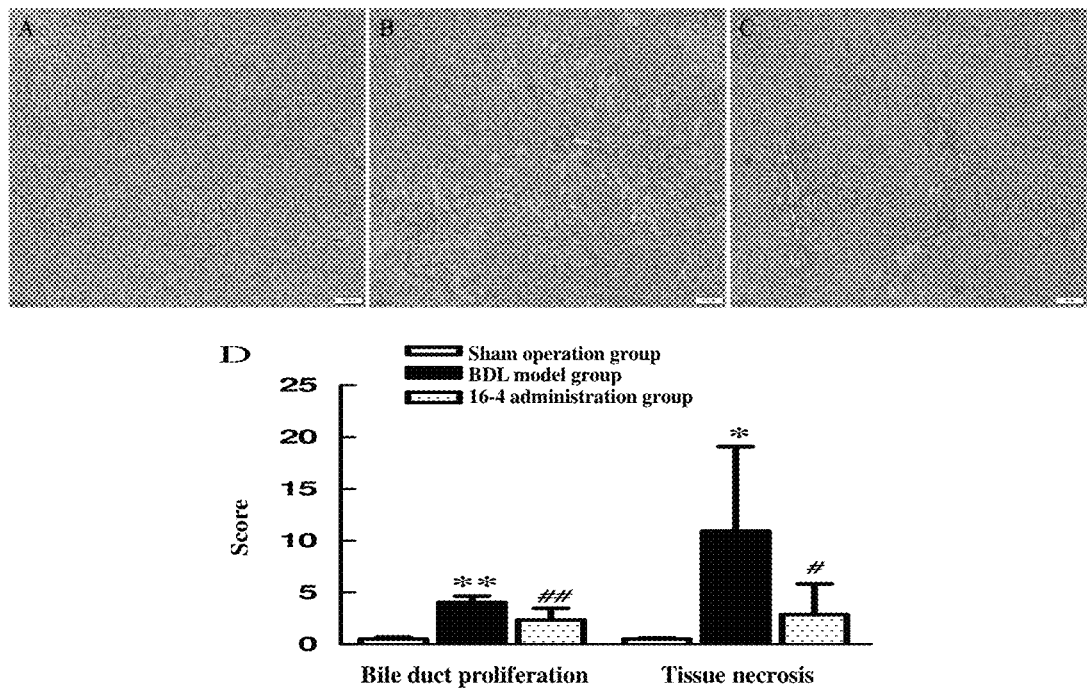
FIG. 7 shows the HE staining results of the liver tissue slices of rats in sham operation group (FIG. 7A), BDL model group (FIG. 7B) and 16-4 administration group (FIG. 7C), and the statistical chart on the double-blind scores of the HE staining of the animal tissues of each group (FIG. 7D) in Example 8. *represents p<0.05 compared to sham operation group; **represents p<0.01 compared to sham operation group; # represents p<0.05 compared to BDL model group; ## represents p<0.01 compared to BDL model group. As shown in the figure, in the liver tissues of rats in sham operation group, the hepatocytes were arranged regularly, and the hepatic lobules were intact, without inflammatory cell infiltration and bile duct proliferation; the liver tissues of rats in BDL group had the pathological structure changed greatly, with significant bile duct proliferation and increased tissue necrosis; the rats in 16-4 administration group had the structure of liver tissues improved significantly, with significantly inhibited bile duct proliferation and significantly reduced tissue necrosis. The results showed that the compound 16-4 could significantly improve the pathological structure of the liver tissues in BDL rats.

FIG. 7A-7C showed the HE staining results of the liver tissue slices of rats in sham operation group, BDL model group and 16-4 administration group, respectively. FIG. 7D was the statistical chart on the double-blind scores of the HE staining of the animal tissues of each group. *represents $p<0.05$ compared to sham operation group; **represents $p<0.01$ compared to sham operation group; # represents $p<0.05$ compared to BDL model group; ## represents $p<0.01$ compared to BDL model group.

The results showed that in the liver tissues of rats in sham operation group, the hepatocytes were arranged regularly, and the hepatic lobules were intact, without inflammatory cell infiltration and bile duct proliferation; the rats in BDL group had the pathological structure of liver tissues changed greatly, with significant bile duct proliferation and significantly increased tissue necrosis; the rats in 16-4 administration group had the structure of liver tissues improved significantly, with significantly inhibited bile duct proliferation and significantly reduced tissue necrosis. The results showed that the compound 16-4 could significantly improve the pathological structure of the liver tissues in BDL rats.

Example 9

In the example, the compound 16-4 was studied for its inhibitory effect on liver fibrosis of BDL model rats.

(1) Masson staining is a collagen fibril-specific staining and can reflect the extent of liver fibrosis in liver tissue. The liver tissue samples were collected from rats of each group in Example 6, and paraffin slices were made. The paraffin slices were stained with Masson's staining solution, and the fibrosis in rat liver tissue was observed.

Figure 8:
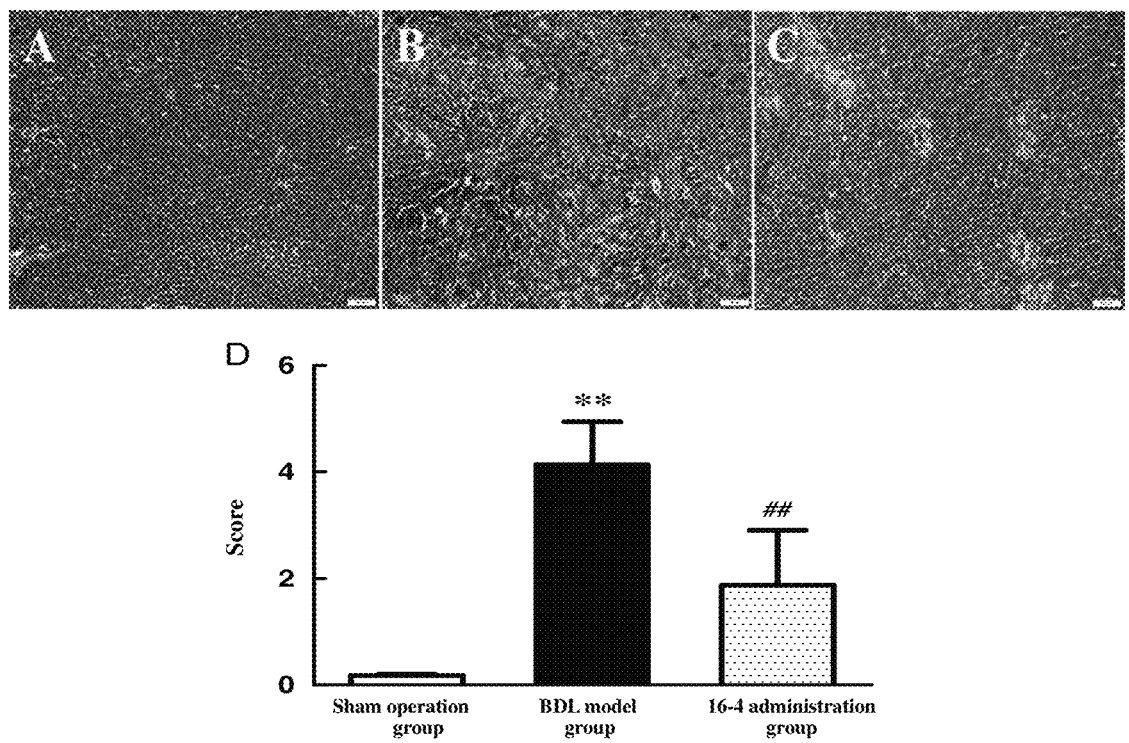
FIG. 8 shows the Masson staining results of the liver tissue slices of rats in sham operation group (FIG. 8A), BDL model group (FIG. 8B) and 16-4 administration group (FIG. 8C), and the statistical chart on the double-blind scores of the Masson staining of the animal tissues of each group (FIG. 8D) in Example 9. **represents p<0.01 compared to sham operation group; ## represents p<0.01 compared to BDL model group. As shown in the figure, the fibrosis increased significantly in the liver tissues of the BDL rats, and the administration of the compound 16-4, the fibrosis could be significantly inhibited in the liver tissues. The results showed that the compound 16-4 could significantly inhibit the production of myofibrils and inhibit liver fibrosis in BDL rats.

FIG. 8A-8C showed the Masson staining results of the liver tissue slices of rats in sham operation group, BDL model group and 16-4 administration group, respectively. FIG. 8D was the statistical chart on the double-blind scores of the Masson staining of the animal tissues of each group. **represents $p<0.01$ compared to sham operation group; ## represents $p<0.01$ compared to BDL model group. The results showed that compared to sham operation group, the fibrosis increased significantly in the liver tissues of the BDL rats, and the compound 16-4 could significantly inhibit the fibrosis of liver tissues. The results showed that the compound 16-4 could significantly inhibit the production of myofibrils, and inhibit liver fibrosis in BDL rats.

(2) Hydroxyproline is specific to collagen fibrils, and the content of hydroxyproline can reflect the extent of liver fibrosis. Liver tissue samples (80-100 mg) were taken from the rats of each group in Example 6, and in accordance with the instruction of Hydroxyproline Assay Kit (purchased from Nanjing Jiancheng Bioengineering Institute), the content of hydroxyproline in the liver tissues was determined.

Figure 9:
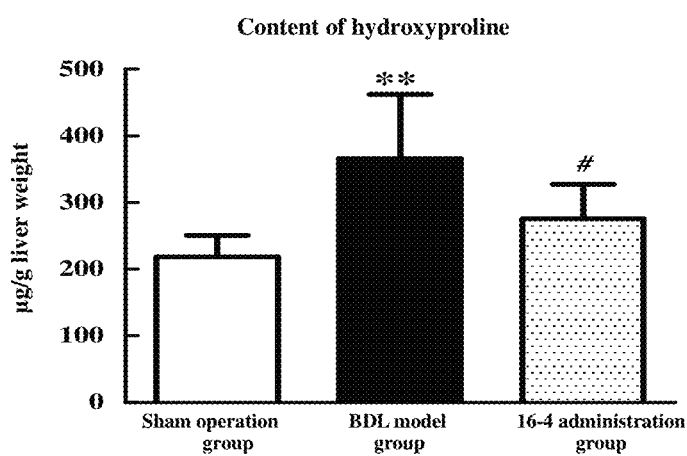
FIG. 9 shows the content of hydroxyproline in liver tissues of rats in sham operation group, BDL model group and 16-4 administration group in Example 9. **represents p<0.01 compared to sham operation group; # represents p<0.05 compared to BDL model group. The results showed that compared to sham operation group, the content of hydroxyproline increased significantly in the liver tissues of BDL model rats; the compound 16-4 could significantly reduce the content of hydroxyproline in rat liver tissues. The results showed that the compound 16-4 could significantly inhibit the production of collagen fibrils and inhibit the occurrence of liver fibrosis.

FIG. 9 showed the content of hydroxyproline in liver tissues of rats in each group. **represents $p<0.01$ compared to sham operation group; # represents $p<0.05$ compared to BDL model group. The results showed that compared to sham operation group, the content of hydroxyproline increased significantly in the liver tissues of BDL model rats; the compound 16-4 could significantly reduce the content of hydroxyproline in rat liver tissues. The results showed that the compound 16-4 could significantly inhibit the production of collagen fibrils, and inhibit the occurrence of liver fibrosis in BDL rats.

Example 10

In the example, the compound 16-4 was studied for its inhibitory effect on markers associated with liver fibrosis in liver tissues of BDL rats.

(1) Assay on expression of genes associated with liver fibrosis in liver tissues by PCR Method.

Liver tissues (80-100 mg) were taken from the rats of each group in Example 6, and 1 mL TRizol was added. The tissues were homogenized in the condition of an ice bath, and centrifuged at 12000 rpm, 4° C. for 10 min. The supernatant was taken, and the total RNA was extracted. According to the operations described in the instruction of Roche Transcriptor First Strand cDNA Synthesis Kit, the total RNA of LX2 was reverse transcribed into cDNA. The cDNA obtained, sterile water, Roche FastStart Universal Probe Master (Rox) and ABI TaqMan probes were used to prepare a 20 μL reaction system, which was analyzed by ABI 7500 Fast Real-Time PCR System.

Figure 10:
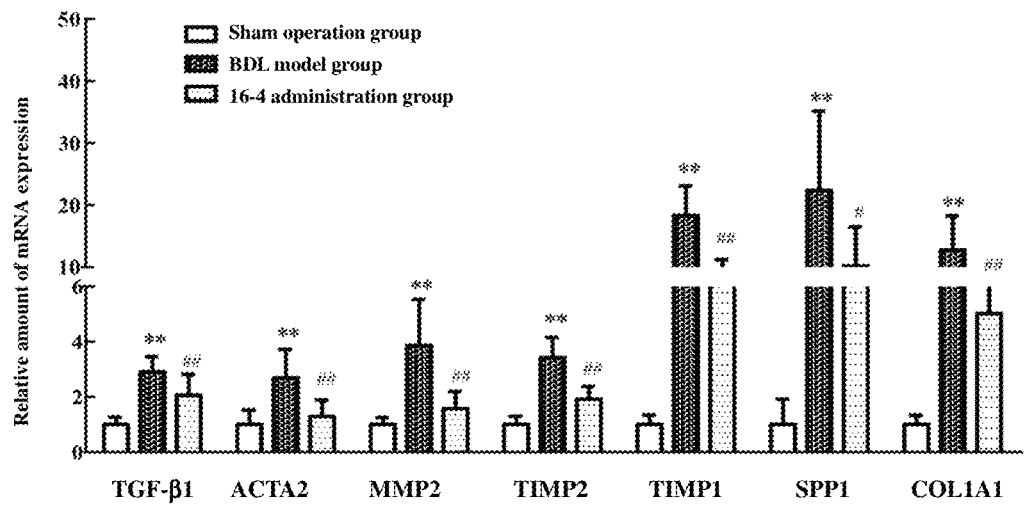
FIG. 10 shows the expression levels of genes associated with liver fibrosis in rat liver tissues determined by real-time PCR method in Example 10. **represents p<0.01 compared to sham operation group; # represents p<0.05 compared to BDL model group, ## represents p<0.01 compared to BDL model group. The results showed that compared to sham operation group, the expression levels of genes associated with liver fibrosis (COL1A1, TGF-β1, MMP2, α-SMA (ACTA2), TIMP1, TIMP2 and SPP1) increased significantly in the liver tissues of rats in BDL model group; the compound 16-4 significantly decreased the expression levels of genes associated with liver fibrosis.

FIG. 10 showed the expression levels of genes associated with liver fibrosis in the liver tissues of rats in sham operation group, BDL model group and 16-4 administration group. **represents $p<0.01$ compared to sham operation group; # represents $p<0.05$ compared to BDL model group, ## represents $p<0.01$ compared to BDL model group. The results showed that compared to sham operation group, the expression levels of genes associated with liver fibrosis (COL1A1, TGF-β1, MMP2, α-SMA (ACTA2), TIMP1, TIMP2 and SPP1) increased significantly in the liver tissues of rats in BDL model group, the administration of the compound 16-4 could significantly reduce the expression of genes associated with liver fibrosis.

(2) Assay on expression of proteins associated with liver fibrosis in liver tissue by Western Blot Liver tissues (80-100 mg) were taken from the rats of each group in Example 6, and 1 mL RAPI lysis solution (containing 1% PMSF) was added. The tissues were homogenized in the condition of an ice bath, and centrifuged at 12000 rpm, 4° C. for 10 min. The supernatant was taken, and the protein concentration was determined by BCA method. The sample was loaded at a concentration of 50 μg/20 μL, subjected to polyacrylamide gel electrophoresis, transferred to a membrane, blocked with 5% skim milk, incubated with a primary antibody, washed with PBST, incubated with a secondary antibody, and imaged with ChemiImager 5500 imaging system.

Figure 11:
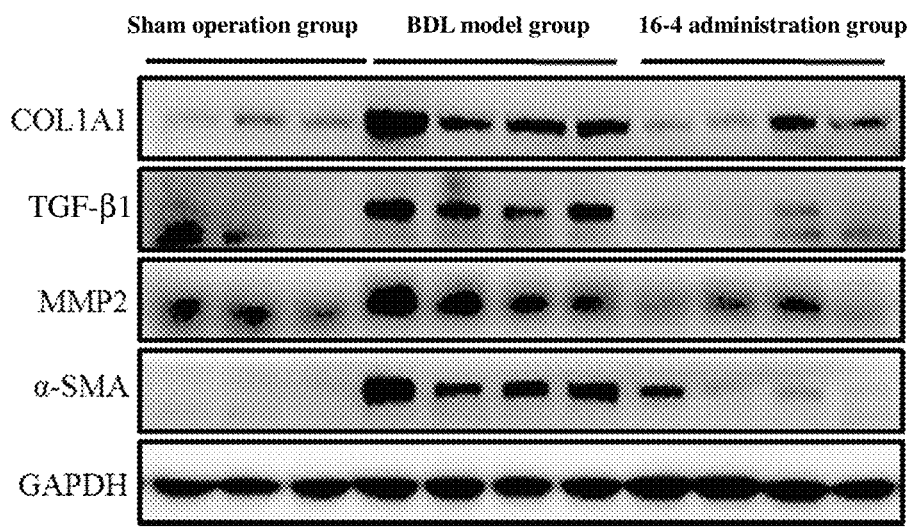
FIG. 11 shows the results on the expression levels of the proteins associated with liver fibrosis in rat liver tissues determined by Western blot in Example 10. The results showed that the compound 16-4 could significantly inhibit the expression of COL1A1, TGF-β1, MMP2 and α-SMA.

FIG. 11 showed the expression levels of proteins associated with liver fibrosis in the liver tissues of rats in sham operation group, BDL model group and 16-4 administration group. The results showed that the compound 16-4 could significantly inhibit the expression of COL1A1, TGF-β1, MMP2 and α-SMA protein.

The experimental results showed that the compound 16-4 could improve the liver function and the pathological structure of liver in rats in BDL model group, reduce the liver fibrosis, and delay the occurrence and development of liver fibrosis.

Although the embodiments of the invention have been described in detail, a person skilled in the art would understand that according to all the disclosed teachings, details can be amended and modified, and these alterations all fall into the protection scope of the invention. The scope of the invention is defined by the attached claims and any equivalent thereof.

The invention claimed is:

1. A method for treating a toxic liver injury, comprising administering an effective amount of a compound of Formula (II) to a subject in need thereof:

2. The method according to claim 1, wherein the compound is selected from:

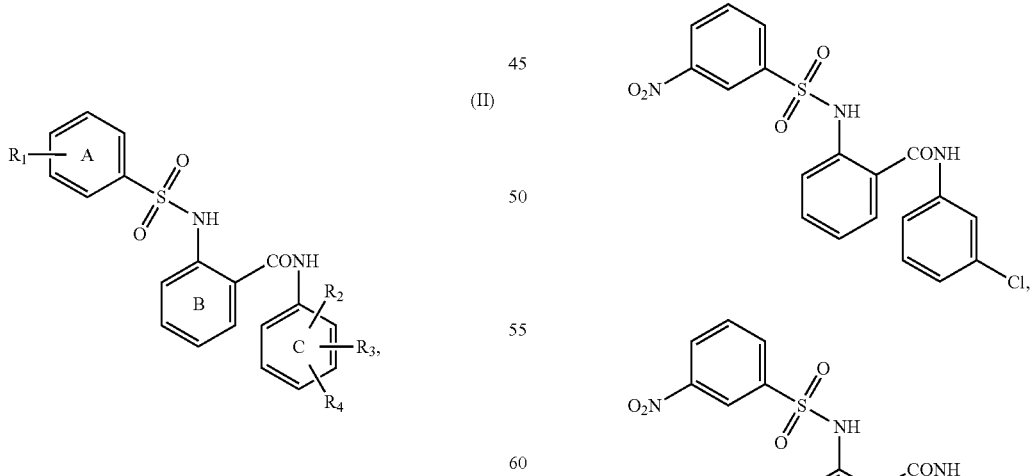

wherein
$R_1$ is at the meta-position of $-SO_2-$;
$R_1$ is $-OCF_3$ or $-NO_2$; and
$R_2$, $R_3$ and $R_4$ are each independently selected from $-H$ and $-Cl$, and, $R_2$, $R_3$ and $R_4$ are not $-H$ simultaneously.

-continued
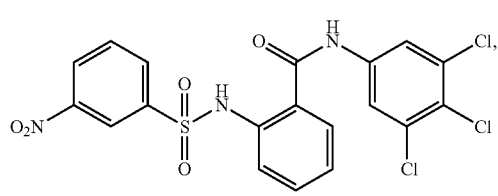
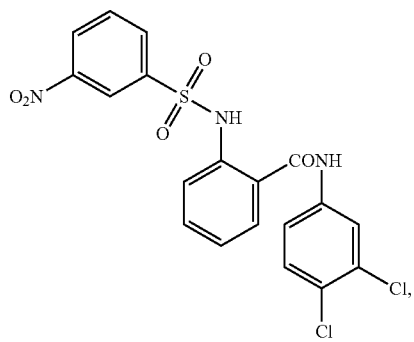
-continued
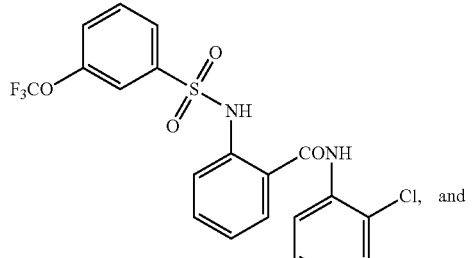
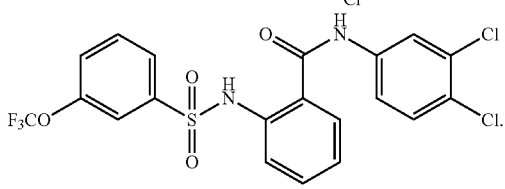
3. The method according to claim 1, wherein the subject is a mammal.
4. The method according to claim 1, wherein the subject is a human.
* * * * *

UNITED STATES PATENT AND TRADEMARK OFFICE
CERTIFICATE OF CORRECTION

PATENT NO. : 10,933,038 B2
APPLICATION NO. : 15/779431
DATED : March 2, 2021
INVENTOR(S) : Hongwei Tian et al.

Page 1 of 1

It is certified that error appears in the above-identified patent and that said Letters Patent is hereby corrected as shown below:

In the Claims

In Claim 2, at Column 49, Lines 14-26, the structure:

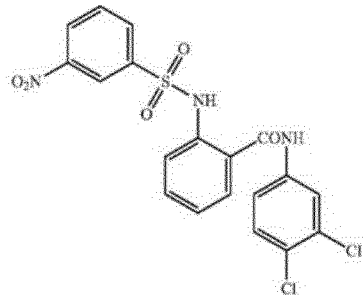

Should be replaced with the structure:

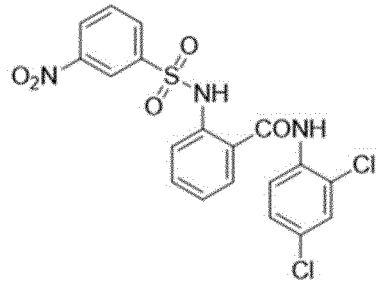

Signed and Sealed this
Eleventh Day of May, 2021

Drew Hirshfeld
*Performing the Functions and Duties of the
Under Secretary of Commerce for Intellectual Property and
Director of the United States Patent and Trademark Office*